(12) United States Patent
Ito et al.

(10) Patent No.: US 7,039,161 B2
(45) Date of Patent: May 2, 2006

(54) METHOD FOR ANALYZING FILM STRUCTURE AND APPARATUS THEREFOR

(75) Inventors: Yoshiyasu Ito, Ome (JP); Kazuhiko Omote, Akiruno (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 10/967,246

(22) Filed: Oct. 19, 2004

(65) Prior Publication Data

US 2005/0105686 A1 May 19, 2005

(30) Foreign Application Priority Data

Oct. 20, 2003 (JP) .............................. 2003-359835

(51) Int. Cl.
*G01N 23/001* (2006.01)
*G01N 23/20* (2006.01)
*G01B 15/02* (2006.01)

(52) U.S. Cl. .............................. 378/86; 378/70; 378/90

(58) Field of Classification Search .................. 378/86, 378/67, 68, 70, 81, 83, 88, 89, 90, 7, 50, 378/53

See application file for complete search history.

(56) References Cited

U.S. PATENT DOCUMENTS

| | | | |
|---|---|---|---|
| 6,192,103 B1 * | 2/2001 | Wormington et al. | 378/73 |
| 6,895,075 B1 * | 5/2005 | Yokhin et al. | 378/90 |
| 6,937,695 B1 * | 8/2005 | Hoshino | 378/86 |
| 2003/0157559 A1 | 8/2003 | Omote et al. | |
| 2004/0195498 A1 | 10/2004 | Omote | |

FOREIGN PATENT DOCUMENTS

| | | |
|---|---|---|
| JP | 2001349849 A * | 12/2001 |
| JP | 2003-14663 | 1/2003 |

* cited by examiner

*Primary Examiner*—Edward J. Glick
*Assistant Examiner*—Irakli Kiknadze
(74) *Attorney, Agent, or Firm*—Wenderoth, Lind & Ponack, L.L.P.

(57) ABSTRACT

A method and apparatus for analyzing a film structure analyze particle or pore size distribution with high accuracy and evaluate a shape of a surface or interface even in the case where the absolute amount of particles or pores in the thin film is small. The method includes fitting a simulated X-ray scattering curve obtained by simulation calculation to a measured X-ray scattering intensity curve obtained by emitting an X-ray onto a surface of a film specimen having a single layer or multi-layer structure at an angle in the vicinity of the critical angle to the surface, by varying at least one parameter characterizing a physical property of the specimen, and obtaining optimum values of parameters providing the minimum difference between the measured X-ray scattering curve and the simulated X-ray scattering curve, so as to determine the structure of the film specimen, in which plural combinations of incident angle and outgoing angle relative to the surface of the film specimen are set so that there is no correlation between the incident angle and the outgoing angle, and the simulated X-ray scattering curve is fitted to the X-ray scattering curve that is obtained by measuring X-ray intensity for the respective combinations of incident angle and outgoing angle.

6 Claims, 29 Drawing Sheets

METHOD FOR ANALYZING FILM STRUCTURE AND APPARATUS THEREFOR

BACKGROUND OF THE INVENTION

1. Field of the Invention

The present invention relates to a method for analyzing a film structure and an apparatus therefor. More particularly, the invention relates to a method for analyzing a film structure for interface roughness and pore distribution of a single layer film or a multi-layer film, and an apparatus therefor.

2. Description of the Related Art

As a method for analyzing the surface and interface of a thin film specimen, a microscope technique using, for example, an electron microscope, is generally employed, and a large amount of information can be obtained with this real-space observation. However, it in fact involves such problems as restriction in observable areas, damage to the specimen, and difficulty in analyzing an interface inside the film.

As nondestructive inspection methods for analyzing a film structure, X-ray reflectivity measurement and X-ray diffuse scattering measurement have been employed.

A method for analyzing a particle diameter distribution of a specimen having an uneven density, such as a porous film, by utilizing X-ray reflectivity measurement has been proposed by the inventor of the present invention (as described in JP-A-2001-349849). In the analyzing method, a diffuse scattering intensity of an X-ray is measured, and a particle diameter distribution is analyzed based on the measured values.

Upon emitting an X-ray at an angle to graze a surface of a thin film, the incident X-ray is reflected and transmitted. At this time, the grazing incident angle is in the vicinity of the total reflection critical angle of the film, and the (penetrating) X-ray can hardly at all penetrate into the interior of the thin film due to the effect of refraction, but proceeds as an evanescent wave beneath the surface of the thin film in a region of several nanometers below the surface. Accordingly, analysis of the surface structure of a thin film is enabled in the case where an X-ray is made grazing incident with an incident condition close to the total reflection critical angle.

A surface or interface of a thin film has an electron density fluctuation (roughness) on the order of several nanometers in the direction normal to the surface of the specimen. Such a method for analyzing a specimen having an uneven density and an apparatus and system therefor have been proposed (in JP-A-2003-14663) that an X-ray transmitted almost parallel to the surface of the specimen creates an X-ray profile corresponding to the shape of the surface or interface of the specimen, the profile then being analyzed to determine the surface or interface shape.

Although excellent analyzing capabilities are realized by the methods for analyzing a specimen having an uneven density using X-rays proposed by the inventors and others, these methods cannot analyze the shape of the interface and the pore size of the specimen simultaneously. Furthermore, they assume that the target of analysis is a single layer film and are difficult to apply to a specimen having a multi-layer structure. Furthermore, in the case where the absolute amount of the particles or pores in the thin film is small. (i.e., the density of the particles or pores per unit volume is small), X-ray scattering due to the roughness of the surface or interface becomes pronounced relative to the scattering due to particles or pores. There is such a problem that the scattering due to surface or interface roughness is due only to the electron densities at the surface, and does not depend on the film thickness.

SUMMARY OF THE INVENTION

The invention has been made under the aforementioned circumstances, and an object thereof is to provide a method for analyzing a film structure and an apparatus therefor that realizes simultaneous analysis of a shape of an interface and a pore size of a specimen, can be applied to a specimen having a multi-layer structure, and can analyze the particle or pore size distribution and evaluate the surface or interface shape with high accuracy even in the case where the absolute amount of the particles or pores is small by utilizing two characteristic features, i.e., that the particle or pore scattering is suddenly increased when the X-ray incident angle becomes larger than the total reflection critical angle, and that the surface or interface scattering is prominent when the X-ray incident angle is from 0° to the total reflection critical angle.

In order to solve the problem described above, the invention relates to, as a first aspect, a method for analyzing a film structure containing steps of: fitting a simulated X-ray scattering curve obtained by simulation calculation to a measured X-ray scattering intensity curve obtained by emitting X-rays onto the surface of a film specimen having a single layer or multi-layer structure at an angle in a vicinity of the critical angle to the surface, by varying at least one parameter characterizing a physical property of the specimen; and obtaining, as optimum values, values of the parameter providing a minimum difference between the measured X-ray scattering curve and the simulated X-ray scattering curve, so as to determine the structure of the film specimen, wherein plural combinations of incident and outgoing angles to the surface of the film specimen are set so that there is no correlation between the incident angle and the outgoing angle, and the simulated X-ray scattering curve is fitted to a measured X-ray scattering curve that is obtained by measuring an X-ray intensity for the respective combinations of an incident angle and an outgoing angle.

The invention also relates to, as a second aspect, a method for analyzing a film structure containing steps of: fitting a simulated X-ray scattering curve obtained by simulation calculation to a measured X-ray scattering intensity curve obtained by emitting X-rays onto a surface of a film specimen having a single layer or multi-layer structure at an angle in the vicinity of the critical angle to the surface, by varying at least one parameter characterizing a physical property of the specimen; and obtaining, as optimum values, values of the parameter providing a minimum difference between the measured X-ray scattering curve and the simulated X-ray scattering curve, so as to determine the structure of the film specimen, the simulated X-ray scattering curve being fitted to a measured X-ray scattering curve that is obtained by at least two of the following three kinds of measurements: offset scan measurement, rocking scan measurement and detector scan measurement.

The invention further relates to, as a third aspect, the method for analyzing a film structure according to the second aspect, wherein the simulated X-ray scattering curve that is obtained by simulation calculation is fitted by varying parameters relating to roughness of the surface of the film specimen and to pore size inside the film specimen to the measured X-ray scattering curve that is obtained by offset scan measurement, obtaining optimum values of the parameters providing a minimum difference between the measured X-ray scattering curve and the simulated X-ray scattering curve, so as to determine the structure of the film specimen.

The invention further relates to, as a fourth aspect, an apparatus for analyzing a film structure containing: means for fitting a simulated X-ray scattering curve obtained by simulation calculation to a measured X-ray scattering intensity curve obtained by making an X-ray incident on a surface of a film specimen having a single layer or multi-layer structure at an angle in a vicinity of a critical angle to the surface, by varying at least one parameter characterizing a physical property of the specimen; and means for obtaining, as optimum values, values of the parameters providing a minimum difference between the measured X-ray scattering curve and the simulated X-ray scattering curve, so as to determine the structure of the film specimen, wherein plural combinations of an incident angle and an outgoing angle to the surface of the film specimen, combined so as to create no correlation between the incident angle and the outgoing angle, are set, and the simulated X-ray scattering curve is fitted to the measured X-ray scattering curve that is obtained by measuring an X-ray intensity for the respective combinations of an incident angle and an outgoing angle.

The invention further relates to, as a fifth aspect, an apparatus for analyzing a film structure containing: means for fitting a simulated X-ray scattering curve obtained by simulation calculation to a measured X-ray scattering intensity curve obtained by emitting X-rays onto a surface of a film specimen having a single layer or multi-layer structure at an angle in a vicinity of the critical angle to the surface, by varying at least one parameter characterizing a physical property of the specimen; and means for obtaining, as optimum values, values of parameters providing a minimum difference between the measured X-ray scattering curve and the simulated X-ray scattering curve, so as to determine the structure of the film specimen, the simulated X-ray scattering curve being fitted to a measured X-ray scattering curve that is obtained by at least two of the following three kinds of measurements: offset scan measurement, rocking scan measurement and detector scan measurement.

The invention further relates to, as a sixth aspect, the apparatus for analyzing a film structure according to the fifth aspect, wherein the simulated X-ray scattering curve that is obtained by simulation calculation carried out by varying parameters relating to roughness of the surface of the film specimen and pore size inside the film specimen is fitted to the measured X-ray scattering curve that is obtained by offset scan measurement, and values of parameters providing a minimum difference between the measured X-ray scattering curve and the simulated X-ray scattering curve are obtained as optimum values, so as to determine the structure of the film specimen.

According to the method for analyzing a film structure and an apparatus therefor of the invention, the shape of an interface and a pore size of a specimen can be simultaneously analyzed, and a specimen having a multi-layer structure can be analyzed.

The effects obtained by the method for analyzing a film structure and an apparatus therefor of the invention will be specifically described below.

(1) In the conventional techniques, the fitting is carried out to a measured X-ray scattering curve obtained by offset scan measurement to analyze a film structure. In the invention, on the other hand, plural combinations of an incident angle and an outgoing angle are set such that there is no correlation between them, the fitting is carried out to the measured X-ray scattering curve that is obtained by measuring an X-ray intensity for the respective combinations of an incident angle and an outgoing angle, or the fitting is carried out to the measured X-ray scattering curve that is obtained by at least two of the following three kinds of measurements: offset scan measurement, rocking scan measurement and detector scan measurement, whereby optimum values of the parameters showing the physical properties of the film specimen can be obtained. In the method for analyzing a film structure and the apparatus therefor according to the invention, a measured X-ray scattering curve obtained by rocking scan measurement is analyzed along with a measured X-ray scattering curve obtained by offset scan measurement, whereby the shape of the interface and the pore size distribution inside the film can be carried out.

(2) In the method for analyzing a film structure according to the invention, a pore size distribution in a multi-layer film can be evaluated.

(3) In a region where the incident angle and the outgoing angle are smaller than the total reflection critical angle, only a signal scattering from the outermost interface is contained in outgoing X-rays, and the shape of the outermost interface can be evaluated by analyzing the measured X-ray scattering curves obtained by plural kinds of rocking scan measurement in the angle region.

(4) In contrast to pore scattering, interface scattering causes interference of scattering among the respective interfaces, and vibrations corresponding to the film thickness are observed. The shapes of the interfaces other than the outermost interface can be evaluated by the amplitudes thereof and the slope of the interference scattering.

(5) In particular, a significant difference is observed between interface scattering and pore scattering in a X-ray scattering curve obtained by rocking scan measurement. Interface scattering is prominent in the vicinity of the specular reflection, this scattering corresponding to the distance correlating to the electron density fluctuation inward from the interface and also corresponding to the shape of the interface. In the pore scattering, on the other hand, a substantially constant scattering intensity is observed in the vicinity of specular reflection. The ratio between the pore scattering and interface scattering can be estimated by utilizing this difference, and both types of scattering can be simultaneously analyzed. This is due to the fact that the shape of the interface scattering has anisotropy between the in-plane direction and the direction perpendicular to the surface. The pore scattering has substantially no anisotropy of this kind since it is present randomly in the film.

(6) In the rocking scan measurement, the pore scattering can be observed provided that an X-ray can penetrate into the film since scatterer bodies (pores) are present inside the film, i.e., the incident angle exceeds the total reflection critical angle. In other words, scattering is suddenly observed when the incident angle of the X-ray exceeds the total reflection critical angle of the porous film. With respect to the roughness of the surface or interface, on the other hand, the interface scattering depends on the intensity of the refraction X-ray (referred to as Yoneda wing) at the interface since a scatterer (roughness) is present at the interface, and it is observed even in the case where the incident angle of the X-ray and the reflection angle of the X-ray are smaller than the total reflection critical angle. The incident angle dependency of the refraction X-ray (Yoneda wing) has a continuous nature and does not suddenly increase. Therefore, the interface scattering and the pore scattering can be discriminated from each other by determining whether or not the scattering intensity is suddenly increased at the total reflection critical angle of the porous film, or by observing the rate that the scattering intensity increases, in the rocking scan measurement.

DESCRIPTION OF THE PREFERRED EMBODIMENTS

Figure 1:
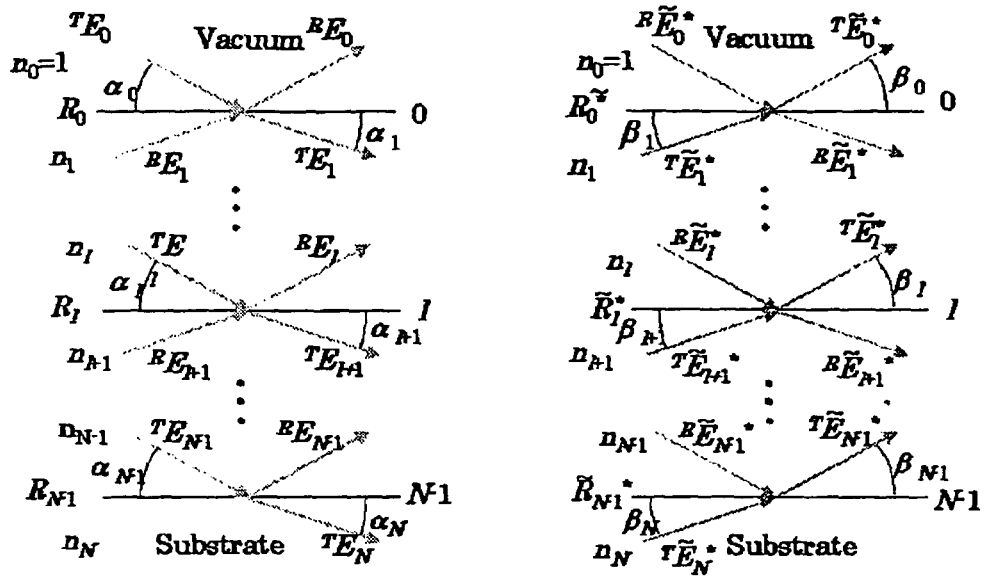
FIG. 1 is a schematic diagram showing eigenstates of an incident wave and an outgoing wave of an X-ray.

In the method for analyzing a film structure according to the invention, a simulated X-ray scattering curve obtained by simulation calculation by varying at least one parameter characterizing a physical property of the specimen is fitted to a measured X-ray scattering intensity curve obtained by emitting X-rays onto a surface of a film specimen at an angle in the vicinity of the critical angle to the surface thereof, and values of parameters whereby the difference between the measured X-ray scattering curve and the simulated X-ray scattering curve is minimum are obtained as optimum values, so as to determine the structure of the film specimen. In the method for analyzing a film structure according to the invention, the film specimen may be a single layer film or a multi-layer film.

In the method for analyzing a film structure according to the invention, plural combinations of an X-ray incident angle and an X-ray outgoing angle to the surface of the film specimen are such that there is no correlation between the incident angle and the outgoing angle, and the fitting is carried out to the measured X-ray scattering curve that is obtained by measuring the X-ray intensity for the respective combinations of an incident angle and an outgoing angle. In the offset scan measurement, the rocking scan measurement and the detector scan measurement, the X-ray incident angle and the X-ray outgoing angle have a particular correlation. In the method for analyzing a film structure according to the invention, however, scan measurement where there is correlation between the X-ray incident angle and the X-ray outgoing angle is not carried out, but rather plural combinations of an X-ray incident angle and an X-ray outgoing angle arbitrarily determined are set, and the fitting is carried out to the X-ray scattering intensities obtained by measuring the respective combinations, so as to determine the structure of the film specimen.

In the detector scan measurement, the incident angle of an X-ray with respect to the surface of the film specimen is maintained at a constant value (i.e., the specimen rotation axis θ is fixed), and the X-ray incident angle is variously changed by scanning the rotation axis 20 of the detector, whereby X-ray intensities at all the incident angles and outgoing angles can be measured.

As the method for analyzing a film structure according to the invention, to which the conventional scan measurement is applied, the following four methods are known.

(1) The fitting is carried out to measured X-ray scattering curves obtained by the offset scan measurement and the rocking scan measurement, with analysis being executed.

(2) The fitting is carried out to measured X-ray scattering curves obtained by the rocking scan measurement and the detector scan measurement, with analysis being executed.

(3) The fitting is carried out to measured X-ray scattering curves obtained by the offset scan measurement and the detector scan measurement, with analysis being executed.

(4) The fitting is carried out to measured X-ray scattering curves obtained by the offset scan measurement, the rocking scan measurement and the detector scan measurement, with analysis being executed.

In the method for analyzing a film structure according to the invention, the fitting for structural analysis is not carried out to plural X-ray intensities that are measured only by using one of the scanning methods and that have correlation between the X-ray incident angle and the X-ray outgoing angle, but rather the X-ray incident angle and the X-ray outgoing angle with respect to the surface of the film specimen are arbitrarily determined completely separately from each other, and the fitting is carried out to plural X-ray intensities measured with the plural combinations of the X-ray incident angle and the X-ray outgoing angle, so as to analyze the film structure.

Upon obtaining the measured X-ray scattering intensity curves, at least two kinds of measurements selected from the offset scan measurement, the rocking scan measurement and the detector scan measurement may be carried out, and fittings may be carried out to each of the measured X-ray scattering curves obtained by the respective kinds of measurement.

As a specific procedure for the fitting, for example, analysis by the method of least squares may be employed, in which a factor from which X-ray reflectivity is calculated is made the parameter, and is changed little by little so as to make minimum the sum of squares of the residuals with respect to the actual reflectivity data, whereby the one set of parameters that best fits the measured data is obtained.

In the analysis by the method of least squares, it may be difficult to minimize the residual sum of squares, depending on the order and method of fitting or appropriateness of the initial value, and the fitting often is not completed due to divergence. It has been known that in the ordinary analysis, if the fitting of simulation data to measured data of X-ray reflectivity is done in the following order the obtained solutions will converge.

(1) A layer structure model of thin layers including a substrate is formed.

(2) The maximum intensity of the simulation data at an angle lower than the critical angle is made equal to that of the measured data.

(3) The background intensity of the model is made equal to the intensity of the measured data.

(4) Parameters to be fixed are selected from the parameters of the model. In many cases, the nature of the substrate glass is known, and therefore, the density thereof is fixed. In the case where other parameters, such as thickness and density, are known, they are determined as constants.

(5) The parameters are manually varied so that simulation data approaches the measured data as confirmed by visual inspection.

(6) Automatic fitting is carried out.

(7) The value of the parameter providing a minimum difference between the measured data and the simulation data is determined to be the optimum value. At this time, if the minimum residual sum of squares is in the second decimal place or less (on the order of $10^{-2}$ or less), it is determined that the fitting is completed with substantial accuracy.

The principals of the simulation calculation carried out upon fitting will be described below.

Definition of Quantum Theory Scattering

Upon making an X-ray graze almost parallel to the surface of a thin film, interference fringes are observed because the incident X-ray and the X-ray reflected at an interface interfere with each other. In the X-ray reflectivity measurement, the interference phenomenon is utilized for evaluating not only the density of the film, but also the thickness of the film and the roughness of the interface. In the method for analyzing a film structure according to the invention, as shown in FIG. 1, in order for scattering at a surface or interface of the specimen under these grazing conditions to be handled as being due to roughness on the surface or the interface of the specimen, the scattering probability is calculated where the scattering potential of the surface/interface roughness acts upon the ground state of X-rays satisfying the reflection and refraction conditions. According to the scattering theory of the quantum mechanics, the differential cross section can be obtained by the following expression where $\Psi_i$ represents the eigenstate of the incident X-ray, $\Psi_f$ represents the eigenstate of the scattered X-ray, and V represents the scattering potential of the surface or interface of the specimen.

$$\frac{d\sigma}{d\Omega} = |\langle \psi_f | V | \psi_i \rangle|^2 \quad \text{(I)}$$

As shown by the expression (I), in order to define the scattering, it is first necessary to determine the eigenstate of the incident X-ray, the eigenstate of the scattered X-ray and the scattering potential.

Eigenstate of X-ray within Film

Calculation of the eigenstate $\Psi$ of the X-ray in the multi-layer film has been made by Parratt. According to the Frenell's formula, the eigenstate of the incident X-ray at the depth $Z_i$ of the first layer film is given by the following expression (II).

$$\psi_i(\alpha)|_l = \prod_{j=1}^{l-1}(\tau_j \varphi_j) e^{ik_0 \eta_l z_l} + \prod_{j=1}^{l-1}(\tau_j \varphi_j)(R_l \varphi_l^2) e^{ik_0 \eta_l z_l} \quad \text{(II)}$$

$$= T_l e^{ik_0 \eta_l z_l} + T_l R_l \varphi_l^2 e^{ik_0 \eta_l z_l}$$

$$\eta_l = \sqrt{n_l - \cos^2 \alpha_0}, \; \gamma_l = \frac{\eta_l - \eta_{l+1}}{\eta_l + \eta_{l+1}} \exp(-2k_0^2 \sigma_l^2 \mathrm{Re}[\eta_l \eta_{l+1}]),$$

$$\tau_l = \frac{2\eta_{l+1}}{\eta_l + \eta_{l+1}}, \; \varphi_l = e^{ik_0 \eta_l \cdot d_l}, \; t_l = \frac{1 - \gamma_l R_l}{\tau_l}$$

$$R_N = 0, \; R_{N-1} = \gamma_{N-1}, \; R_l = \frac{R_{l+1} \varphi_{l+1}^2 + \gamma_l}{R_{l+1} \varphi_{l+1}^2 \gamma_l + 1}$$

With respect to the scattered X-rays, it is necessary to consider the outgoing wave upon scattering at the surface or interface of the specimen. As a solution of such a wave equation, a solution obtained by time reversal of the solution (eigenstate) of the incident X-ray is considered, which is obtained by the following expression (III), obtained by taking the complex conjugate of the solution of the incident X-ray and making k→−k.

$$\tilde{\psi}_f(\varphi)|_l = \prod_{j=1}^{l-1}(\tilde{t}_j^*\tilde{\varphi}_j^*)e^{-ik_0\zeta_l^*z_l} + \prod_{j=1}^{l-1}(\tilde{t}_j^*\tilde{\varphi}_j^*)(\tilde{R}_l^*\tilde{\varphi}_l^{*2})e^{ik_0\zeta_l^*z_l} \quad \text{(III)}$$

$$= \tilde{T}_l^* e^{-ik_0\zeta_l^*z_l} + \tilde{T}_l^*\tilde{R}_l^*\tilde{\varphi}_l^{*2}e^{ik_0\zeta_l^*z_l}$$

$$\zeta_l = \sqrt{n_l - \cos^2\beta_0},\ \tilde{\gamma}_l^* = \frac{\zeta_l^* - \zeta_{l+1}^*}{\zeta_l^* - \zeta_{l+1}^*}\exp(-2k_0^2\sigma_l^2\mathrm{Re}[\zeta_l^*\zeta_{l+1}^*]),$$

$$\tilde{t}_l^* = \frac{2\zeta_{l+1}^*}{\zeta_l^* + \zeta_{l+1}^*},\ \tilde{\varphi}_l^* = e^{-ik_0\zeta_l^*d_l},\ \tilde{t}_l^* = \frac{1 - \tilde{\gamma}_l^*\tilde{R}_l^*}{\tilde{t}_l^*}$$

$$\tilde{R}_N^* = 0,\ \tilde{R}_{N-1}^* = \tilde{\gamma}_{N-1}^*, \ldots, \tilde{R}_l^* = \frac{\tilde{R}_{l+1}^*\tilde{\varphi}_{l+1}^{*2} + \tilde{\gamma}_l^*}{\tilde{R}_{l+1}^*\tilde{\varphi}_{l+1}^{*2}\tilde{\gamma}_l^* + 1}, \ldots$$

Surface or Interface Scattering Process in Film

The surface or interface scattering occurring in the course of multiple reflections in the film is a complex process. Various scattering processes are observed, and some of them are clearly observed only in the vicinity of the total reflection critical angle of the film, and others are clearly observed over a wide range of angles. FIGS. 2A to 2D show the four-component scattering process observed in the respective layers.

Figure 2:
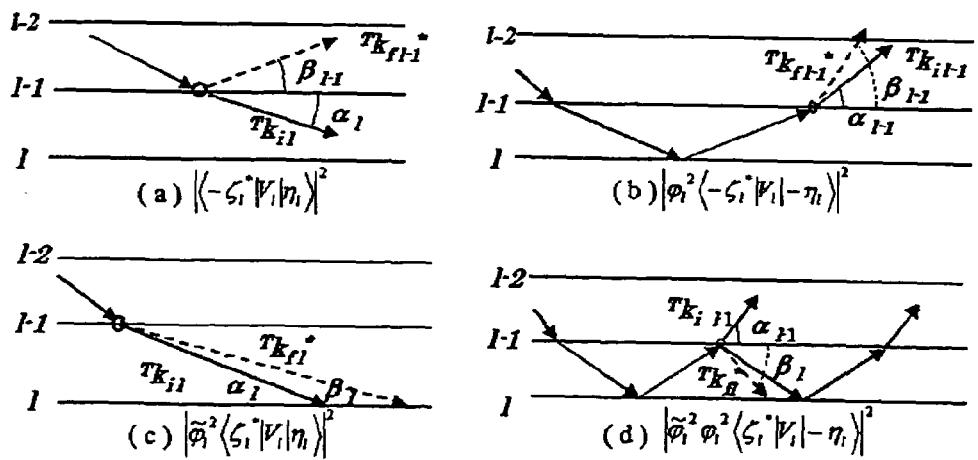
FIGS. 2A to 2D are schematic diagrams showing scattering processes of interface scattering in a film.

FIG. 2A shows a case where an X-ray refracted at an interface I-1 is scattered and immediately observed, hereinafter referred to as scattering process (a). FIG. 2B shows a case where an X-ray which is reflected at an interface I is scattered and then observed, hereinafter referred to as scattering process (b). FIG. 2C shows a case where a scattered X-ray is specularly reflected at an interface I and observed, hereinafter referred to as scattering process (c). FIG. 2D shows a case where an X-ray specularly reflected at an interface I is scattered, and the scattered X-ray is again specularly reflected at the interface I and observed, hereinafter referred to as scattering process (d). The scattering processes (b) to (d), except for that shown by FIG. 2A, contain an effect of reflection at the interface I, and therefore, the X-ray is strongly observed only in the case where the interface I satisfies conditions for specularreflection. On the other hand, the process shown in FIG. 2A contains no contribution of reflection at the interface I, and therefore, these X-rays are observed over a wide range of angles.

Scattering Vector depending on Surface or Interface Scattering Process in Film

As shown in FIGS. 2A to 2D, there are two kinds of the scattering vector $q_s$ orthogonal to the surface generated by surface or interface scattering. The component of the scattering vector orthogonal to the surface generated at the interface I-1 is given below.

The component of the scattering vector orthogonal to the surface in the scattering process (a) and the scattering process (d) are given by the following expression (IV).

$$q_{zl}^+ = k_0 \mathrm{Re}[\eta_l + \zeta_l] \quad \text{(IV)}$$

The component of the scattering vector orthogonal to the surface in the scattering process (b) and the scattering process (c) are given by the following expression (V).

$$q_{zl}^- = k_0 |\mathrm{Re}[\eta_l - \zeta_l]| \quad \text{(V)}$$

The component of the scattering vector in the in-plane direction $q_r$ does not depend on the interfaces or the scattering processes and can be given by the following expression (VI).

$$q_r = k_0 |\cos\beta_0 - \cos\alpha_0| \quad \text{(VI)}$$

Description of Differential Scattering Cross Section

With the surface or interface scattering potential in the first layer expressed as $V_1$, the scattering amplitude in the first layer is given by the following expression (VII), taking into consideration the four scattering processes shown in FIGS. 2A to 2D.

$$\langle\psi_f^l|V_l|\psi_i^l\rangle_l = \tilde{T}_l T_l \langle-\zeta_l^*|V_l|\eta_l\rangle + \tilde{T}_l T R_l \varphi_l^2 \langle-\zeta_l^*|V_l|-\eta_l\rangle + \quad \text{(VII)}$$
$$\tilde{T}_l\tilde{R}_l\tilde{\varphi}_l^2 T\langle\zeta_l^*|V_l|\eta_l\rangle + \tilde{T}_l\tilde{R}_l\tilde{\varphi}_l^2 TR_l\varphi_l^2\langle\zeta_l^*|V_l|-\eta_l\rangle$$

The total scattering amplitude is a sum of the scattering amplitudes in all the layers and is given by the following expression (VIII).

$$\langle\psi_f|V|\psi_i\rangle_{Total} = \sum_{l=0}^{N}\langle\psi_f^l|V_l|\psi_i^l\rangle_l \quad \text{(VIII)}$$

According to the expressions (I) and (VIII), the scattering cross section can be obtained by the following expression (IX).

$$\frac{d\sigma}{d\Omega} = |\langle\psi_f|V|\psi_i\rangle_{Total}|^2 = \left|\sum_{l=0}^{N}\langle\psi_f^l|V_l|\psi_i^l\rangle_l\right|^2 \quad \text{(IX)}$$

$$= \sum_{l=0}^{N}|\langle\psi_f^l|V_l|\psi_i^l\rangle_l|^2 + \sum_{l\neq k}^{N}\langle\psi_f^l|V_l|\psi_i^l\rangle_l^*\langle\psi_f^k|V_k|\psi_i^k\rangle_k$$

The second term of the expression (IX) corresponds to interference scattering occurring among the interfaces. Scattering by Surface/Interface Roughness In the case where roughness is present, in comparison to an ideally flat interface additional scattering is observed corresponding to the change in electron density at the interface and the configuration of interface roughness. The eigenstates of the X-ray before and after scattering are strictly given by the expressions (II) and (III), respectively. The scattering amplitudes caused by the roughness at the interfaces can be calculated by the expression (XII). At this time, in the scattering process shown in FIGS. 2A to 2D, the scattering potential $V_I$ is given by the following expression (X) in the case of the scattering process (a) or the scattering process (c), or by the next expression (XI) in the case of the scattering process (b) or the scattering process (d).

$$V_l = k_0^2(n_{l-1}^2 - n_l^2) \quad \text{(X)}$$

$$V_l = k_0^2(n_l^2 - n_{l-1}^2) \quad \text{(XI)}$$

wherein n represents the refractive indices at the interfaces, and $k_0$ represents the wave number vector in vacuum.

The scattering expression to be defined in the invention is the differential scattering cross section of the following expression (IX). In order to define the differential scattering cross section, it is necessary to calculate scattering amplitudes of the scattering processes of each of the interfaces. If the scattering amplitude can be determined, this is equivalent to determining the differential scattering cross section.

The scattering amplitude occurring in the scattering process (a) at the interface I is derived by the following expression (XII).

$$\tilde{T}_l T_l \langle -\zeta_l^* |V_l| \eta_l \rangle = \tilde{T}_l T_l k_0^2 \int_V (n_{l-1}^2 - n_l^2) e^{iq_l \cdot r} dV \quad \text{(XII)}$$

$$q_l = q_{zl} e_z q_r e_r$$

$$q_{zl} = -k_0 \text{Re}[\eta_l + \zeta_l] \quad q_r = k_0(\cos\beta - \cos\alpha)$$

In order to calculate the surface scattering, the volume component is replaced by the surface integral as in the expression (XIII).

$$\tilde{T}_l T_l \langle -\zeta_l^* |V_l| \eta_l \rangle = \tilde{T}_l T_l k_0^2 (n_{l-1}^2 - n_l^2) \frac{1}{q \cdot A} \int_S e^{iq \cdot r} A \cdot dS \quad \text{(XIII)}$$

wherein dS represents a differential surface vector perpendicular to the surface, and A represents an arbitrary unit vector. Herein, A is taken to be orthogonal to the surface of the specimen. By so doing, the expression (XIII) can be changed to the following expression (XIV).

$$\tilde{T}_l T_l \langle -\zeta_l^* |V_l| \eta_l \rangle = \tilde{T}_l T_l k_0^2 (n_{l-1}^2 - n_l^2) \frac{1}{q_{zl}} \int_S e^{iq \cdot r} dS \quad \text{(XIV)}$$

Calculation using the expression (XIV) can be done in the case where the surface has a particular shape, but in many cases, the electron density fluctuation at the surface or interface is assumed to conform to a certain correlation function and thus is characterized as $|\langle -\zeta_I^* |V_I| \eta_I \rangle|^2$ (described in detail in Shinba, Phys. Rev., vol. B38, p. 2297 (1998)).

$$|\langle -\zeta_l^* |V_l| \eta_l \rangle|^2 = \quad \text{(XV)}$$

$$\frac{2\pi}{q_{zl}^2} |V_l|^2 e^{-q_{zl}^2 \sigma_l^2} \int_0^\infty R \cdot \left[\exp\left(q_{zl}^2 \sigma_l^2 e^{-(R/\xi_l)^{2h_l}}\right) - 1\right] J_0(q_r R) dR$$

wherein σ represents the surface/interface roughness, ζ represents the correlation distance in the in-plane direction of the surface/interface roughness. h represents a Hurst parameter giving the shape of the surface roughness. In the case where h is closer to 1, a smoother surface is given, and in the case where h is closer to 0, a rougher surface is given.

The value $\langle -\zeta_I^* |V_I| \eta_I \rangle$ of the surface/interface roughness cannot be calculated since the surface does not have a particular shape, but $|\langle -\zeta_I^* |V_I| \eta_I \rangle|^2$ can be obtained from the expression (XV). According to the expressions (XIV) and (XV), the scattering amplitude (a) at the interface I in the scattering process (a) can be obtained by the following expression (XVI).

$$\tilde{T}_l T_l \langle -\zeta_l^* |V_l| \eta_l \rangle = \tilde{T}_l T_l k_0^2 (n_{l-1}^2 - n_l^2) \frac{1}{q_{zl}} \sqrt{S(q_{zl}, q_r, \sigma_l, \xi_l, h_l)} \quad \text{(XVI)}$$

$$S(q_{zl}, q_r, \sigma_l, \xi_l, h_l) =$$

$$2\pi e^{-q_{zl}^2 \sigma_l^2} \int_0^\infty R \cdot \left[\exp\left(q_{zl}^2 \sigma_l^2 e^{-(R/\xi_l)^{2h_l}}\right) - 1\right] J_0(q_r R) dR$$

$$q_{zl} = -k_0 \text{Re}[\eta_l + \zeta_l], \quad q_r = k_0(\cos[\beta] - \cos[\alpha])$$

Similarly, the scattering amplitudes (b), (c) and (d) at the interface I can be obtained as in the following expressions (XVII), (XVIII) and (XIX).

$$\tilde{T}_l T R_l \varphi_l^2 \langle -\zeta_l^* |V_l| -\eta_l \rangle = \quad \text{(XVII)}$$

$$\tilde{T}_l T R_l \varphi_l^2 k_0^2 (n_l^2 - n_{l+1}^2) \frac{1}{q_{zl}} \sqrt{S(q_{zl}, q_r, \sigma_l, \xi_l, h_l)}$$

$$S(q_{zl}, q_r, \sigma_l, \xi_l, h_l) =$$

$$2\pi e^{-q_{zl}^2 \sigma_l^2} \int_0^\infty R \cdot \left[\exp\left(q_{zl}^2 \sigma_l^2 e^{-(R/\xi_l)^{2h_l}}\right) - 1\right] J_0(q_r R) dR$$

$$q_{zl} = k_0 \text{Re}[\zeta_l - \eta_l], \quad q_r = k_0(\cos[\beta] - \cos[\alpha])$$

$$\tilde{T}_l \tilde{R}_l \tilde{\varphi}_l^2 T \langle \zeta_l^* |V_l| \eta_l \rangle = \quad \text{(XVIII)}$$

$$\tilde{T}_l \tilde{R}_l \tilde{\varphi}_l^2 T k_0^2 (n_{l+1}^2 - n_l^2) \frac{1}{q_{zl}} \sqrt{S(q_{zl}, q_r, \sigma_l, \xi_l, h_l)}$$

$$S(q_{zl}, q_r, \sigma_l, \xi_l, h_l) =$$

$$2\pi e^{-q_{zl}^2 \sigma_l^2} \int_0^\infty R \cdot \left[\exp\left(q_{zl}^2 \sigma_l^2 e^{-(R/\xi_l)^{2h_l}}\right) - 1\right] J_0(q_r R) dR$$

$$q_{zl} = k_0 \text{Re}[\eta_l - \zeta_l], \quad q_r = k_0(\cos[\beta] - \cos[\alpha])$$

$$\tilde{T}_l \tilde{R}_l \tilde{\varphi}_l^2 T R_l \varphi_l^2 \langle \zeta_l^* |V_l| -\eta_l \rangle = \quad \text{(XIX)}$$

$$\tilde{T}_l \tilde{R}_l \tilde{\varphi}_l^2 T R_l \varphi_l^2 k_0^2 (n_{l+1}^2 - n_l^2) \frac{1}{q_{zl}} \sqrt{S(q_{zl}, q_r, \sigma_l, \xi_l, h_l)}$$

$$S(q_{zl}, q_r, \sigma_l, \xi_l, h_l) =$$

$$2\pi e^{-q_{zl}^2 \sigma_l^2} \int_0^\infty R \cdot \left[\exp\left(q_{zl}^2 \sigma_l^2 e^{-(R/\xi_l)^{2h_l}}\right) - 1\right] J_0(q_r R) dR$$

$$q_{zl} = k_0 \text{Re}[\eta_l + \zeta_l], \quad q_r = k_0(\cos[\beta] - \cos[\alpha])$$

Using the scattering amplitudes derived as above and the expressions (VII) to (IX), the differential scattering cross section is obtained.

In the method for analyzing a film structure according to the invention, the simulation calculation of the interface scattering of an X-ray is carried out by using the aforementioned principles.

In the method for analyzing a film structure according to the invention, as having been described, three kinds of measurements, i.e., the offset scan measurement, the rocking scan measurement and the detector scan measurement, are carried out, X-ray scattering intensity curves are obtained, and the fitting to the measured X-ray scattering curves obtained by the respective kinds of measurements is carried out.

With the measured X-ray scattering curve obtained by the offset scan measurement, simulation calculation is carried out by varying parameters relating to the interface roughness of the surface of the film specimen and the pore size in the film specimen, and a simulated X-ray scattering curve obtained by the simulation calculation is fitted to the measured X-ray scattering curve to obtain the optimum value of the parameter providing the minimum difference between the measured X-ray scattering curve and the simulated X-ray scattering curve, whereby the structure of the film specimen is determined.

The rocking scan measurement is carried out with plural scanning angles different from each other, and a simulated X-ray scattering curve is fitted to the measured X-ray scattering curves obtained in the respective rocking measurements at each angle to obtain, as an optimum value, a value of the parameter providing the minimum difference between the measured X-ray scattering curve and the simulated X-ray scattering curve, whereby the structure of the film specimen is determined. At this time, the optimum value of the parameter relating to the pore size in the film specimen can be obtained by fitting the simulated X-ray scattering curve to measured X-ray scattering curves obtained in the range from the total reflection critical angle on the incident side of the surface of the film specimen to the total reflection critical angle on the outgoing side of the surface of the film specimen. The optimum value of the parameter relating to the interface roughness of the surface of the film specimen can be obtained by fitting the simulated X-ray scattering curve to measured X-ray scattering curves obtained within angles lower than the total reflection critical angle on the incident side on the surface of the film specimen or angles exceeding the total reflection critical angle on the outgoing side on the surface of the film specimen.

A constitution of an apparatus for carrying out the method for analyzing a film structure according to the invention and procedures therefor will be described below.

Figure 3:
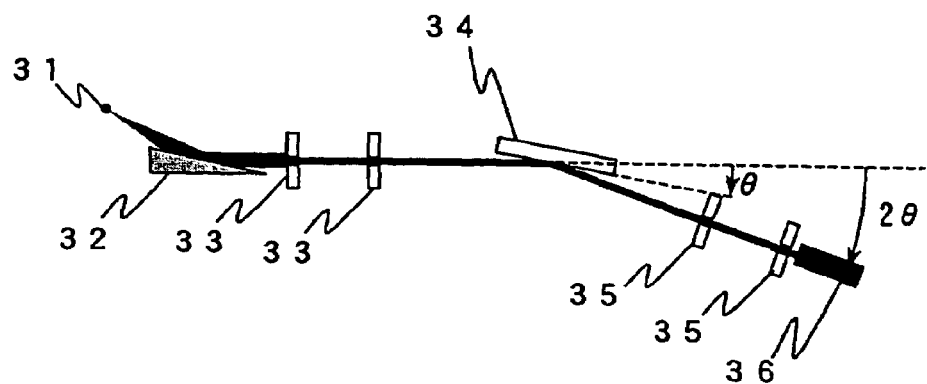
FIG. 3 is a schematic diagram showing an example of a constitution of an optical system of an apparatus for analyzing a film structure according to the invention.

FIG. 3 is a schematic diagram showing an optical system of an apparatus for carrying out the method for analyzing a film structure according to the invention. On the incident side, X-rays emitted from a radiation source 31 are reflected by a multi-layer mirror 32, and the beam diameter thereof is narrowed by two narrowing slits 33. The X-ray incident on a specimen 34 is reflected, refracted and scattered thereon, and then received by detecting means 36 through two narrowing slits 35 provided on the receiving side. The resolution on the side of the detecting means 36 can be improved by using the narrowing slits 35.

The apparatus for analyzing a film structure according to the invention has at least the aforementioned constitution, and in a practical embodiment, the apparatus has, in addition to the aforementioned optical system, means for analyzing a film structure, such as a computer that inputs measurement data obtained through the optical system and analyzing the film structure by using the data thus inputted.

Specific procedures for carrying out the method for analyzing a film structure according to the invention will be described in detail.

The offset angle is estimated by carrying out offset scan measurement with the incident angle and the outgoing angle of an X-ray changed by a certain angle at a time. At this time, the offset angle is set to such an angle where there is no influence of specular reflection. The offset angle can be obtained by rocking scan of specular reflection carried out by scanning the specimen stage angle θ within a certain range while keeping detector stage angle 2θ fixed. The half value width of the specular reflection of the X-ray scattering curve obtained by rocking scan measurement can be calculated by the slit conditions on the receiving side. The approximate divergent angle on the receiving side is given by the following expression (XX) where RSW represents the X-ray receiving slit width on the receiving side, SSW represents the scattering suppressing slit width, RSW is equal to SSW, and L represents the distance from the center of the specimen to the scattering suppressing slit.

$$Angle^{rec} = \frac{360}{\pi}\tan^{-1}\left(\frac{SSW}{2L}\right)\Big/\text{Degree} \quad (XX)$$

Figure 4:
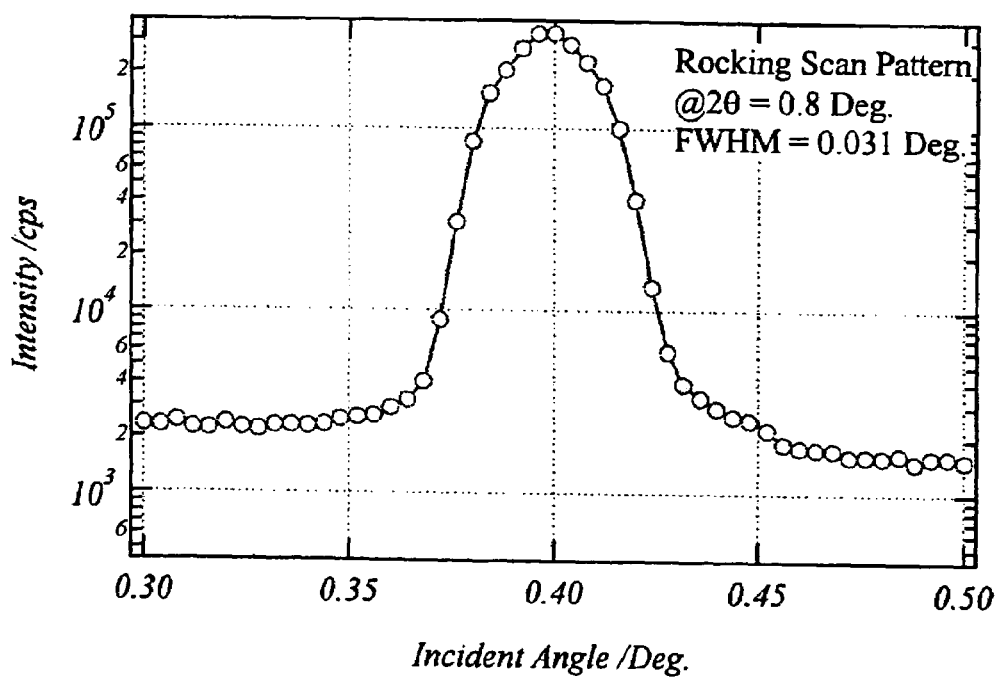
FIG. 4 is a graph showing an X-ray scattering curve obtained by rocking scan measurement carried out for estimating an offset angle.

For example, in the case of RSW=0.2 mm, SSW=0.2 mm, and L=340 mm, the resolution on the receiving side calculated using expression (XX) is about 0.03°. In practice, owing to the influence of the surface of the film specimen, it is necessary to set such an offset angle that does not suffer influence of specular reflection taking into account the measurement result of the specular reflection in the rocking scan as shown in FIG. 4. In the case shown in FIG. 4, the offset angle is estimated as 0.1°, and it is clear that at this setting there is substantially no influence of specular reflection.

Next, offset scan measurement is carried out by moving the detector stage angle 2θ and the specimen stage angle θ with the ratio 2θ/θ kept at 2/1 while the offset angle that has been set as above is kept constant. In the offset scan measurement, since the offset angle is set as small as possible, the in-plane scattering vector is much smaller than the scattering vector orthogonal to the surface of the specimen. Therefore, the interface scattering data mainly reflects the correlation distance of electron density fluctuation orthogonal to the surface of the specimen, i.e., roughness information. The similar situation can be applied to the pore scattering, so that the information reflects size of pores in the direction of the surface of the specimen. However, in the case where the configuration of the pores in the film is different from the configuration of the interface, and there is no large anisotropy between the in-plane direction and the direction orthogonal to the plane, the information reflects average pore size in the film.

Figure 5:
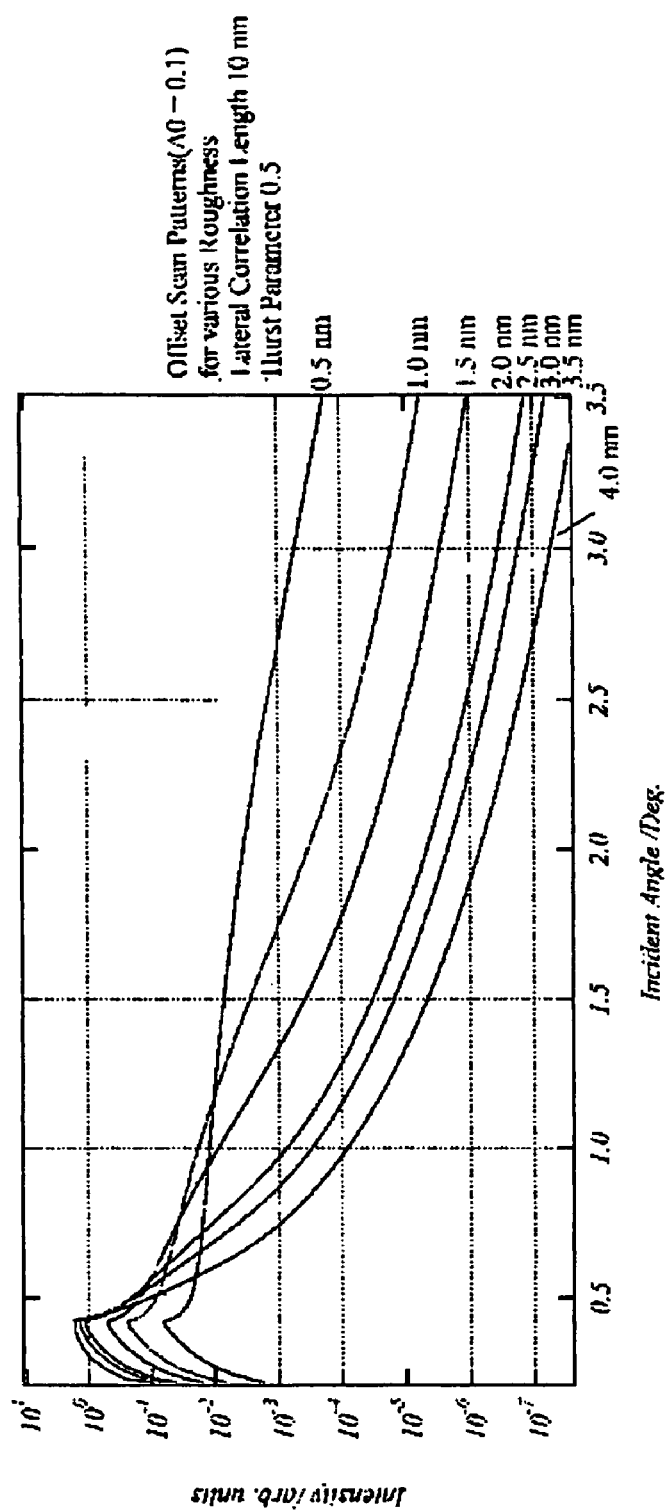
FIG. 5 is a graph showing component simulated X-ray scattering curves by interface scattering obtained by offset scan.
Figure 6:
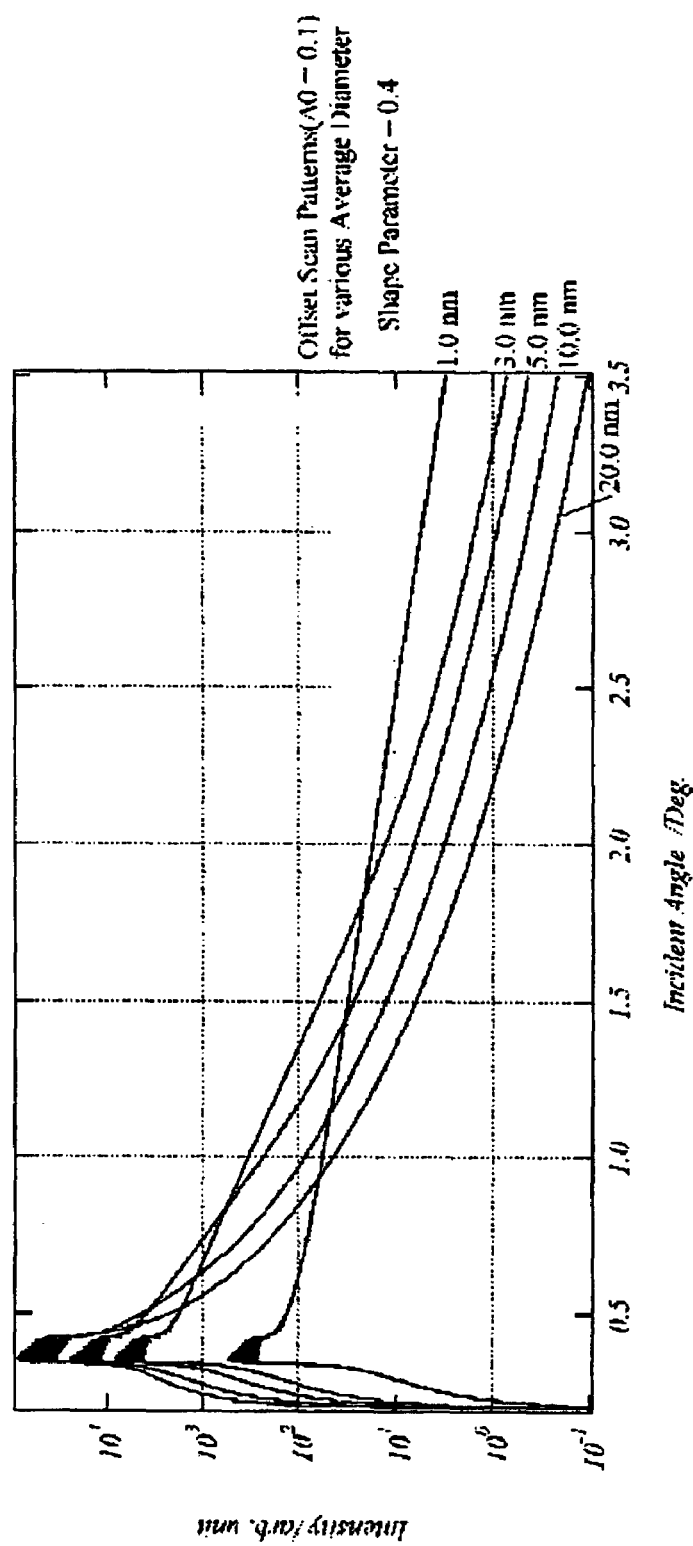
FIG. 6 is a graph showing component-simulation X-ray scattering curves by pore scattering obtained by offset scan.
Figure 7:
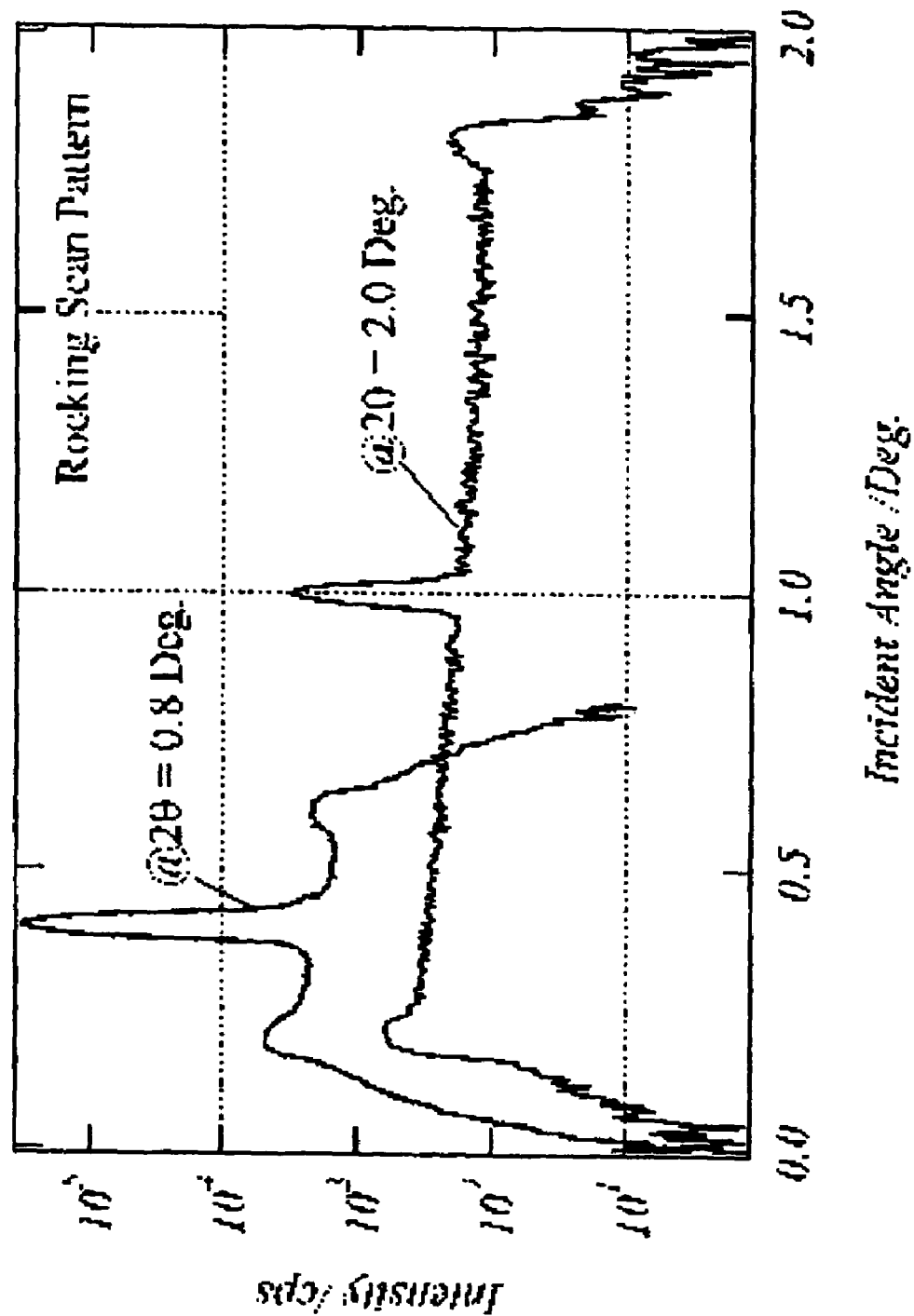
FIG. 7 is a graph showing measured X-ray scattering curves obtained by rocking scan measurement.

Accordingly, the information of the roughness on the interface and the information of the average pore size in the film can be obtained with the X-ray scattering curve obtained by offset scan measurement. As shown in FIG. 5, in the case where the roughness on the interface (the correlation distance of electron density fluctuation orthogonal to the surface of the specimen) is increased, the slope of the X-ray scattering curve of offset scan is increased. As shown in FIG. 6, similarly, in the case where the average pore size in the film is increased, the slope of the X-ray scattering curve of offset scan is increased.

In the rocking scan measurement, the scattering vector orthogonal to the surface of the specimen is substantially constant since the angle of the detector is fixed. On the other hand, the scattering vector in the in-plane direction of the surface of the specimen greatly varies. Accordingly, the information of interface scattering mainly reflects the correlation distance of electron density fluctuation and shape parameters in the in-plane direction of the surface of the specimen.

Figure 8:
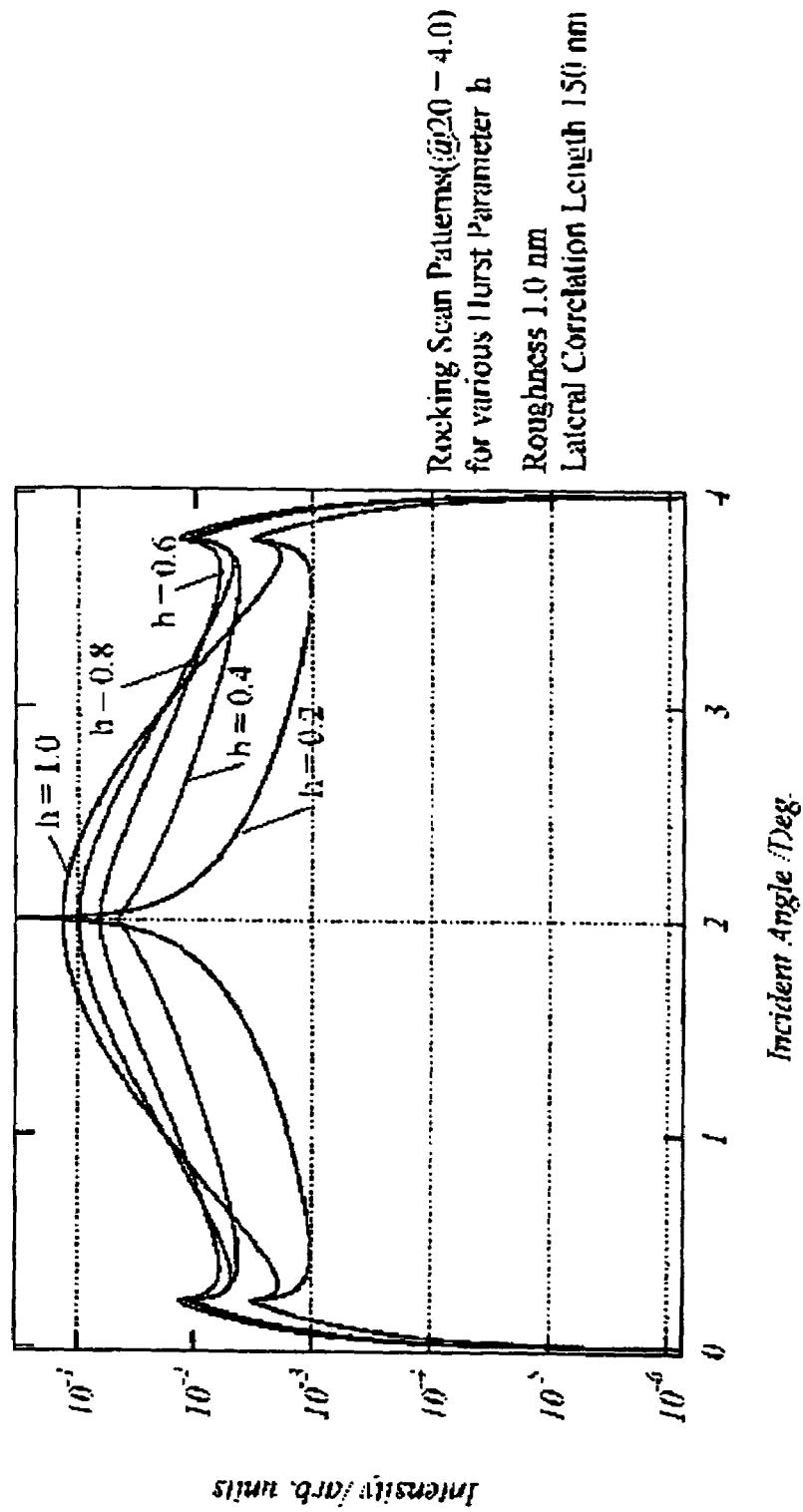
FIG. 8 is a graph showing simulated X-ray scattering curves fitted to rocking scan measurements, varying the shape by changing the Hurst parameter.

FIG. 8 shows simulated X-ray scattering curves obtained by rocking scan measurement in the case where the Hurst parameter, taken here to be the shape parameter, is changed. The X-ray scattering curve becomes a Gaussian curve by setting the Hurst parameter to be a large value. It is also seen that the scattering intensity rapidly increases in the vicinity of specular reflection when the Hurst parameter is set to a small value.

Figure 9:
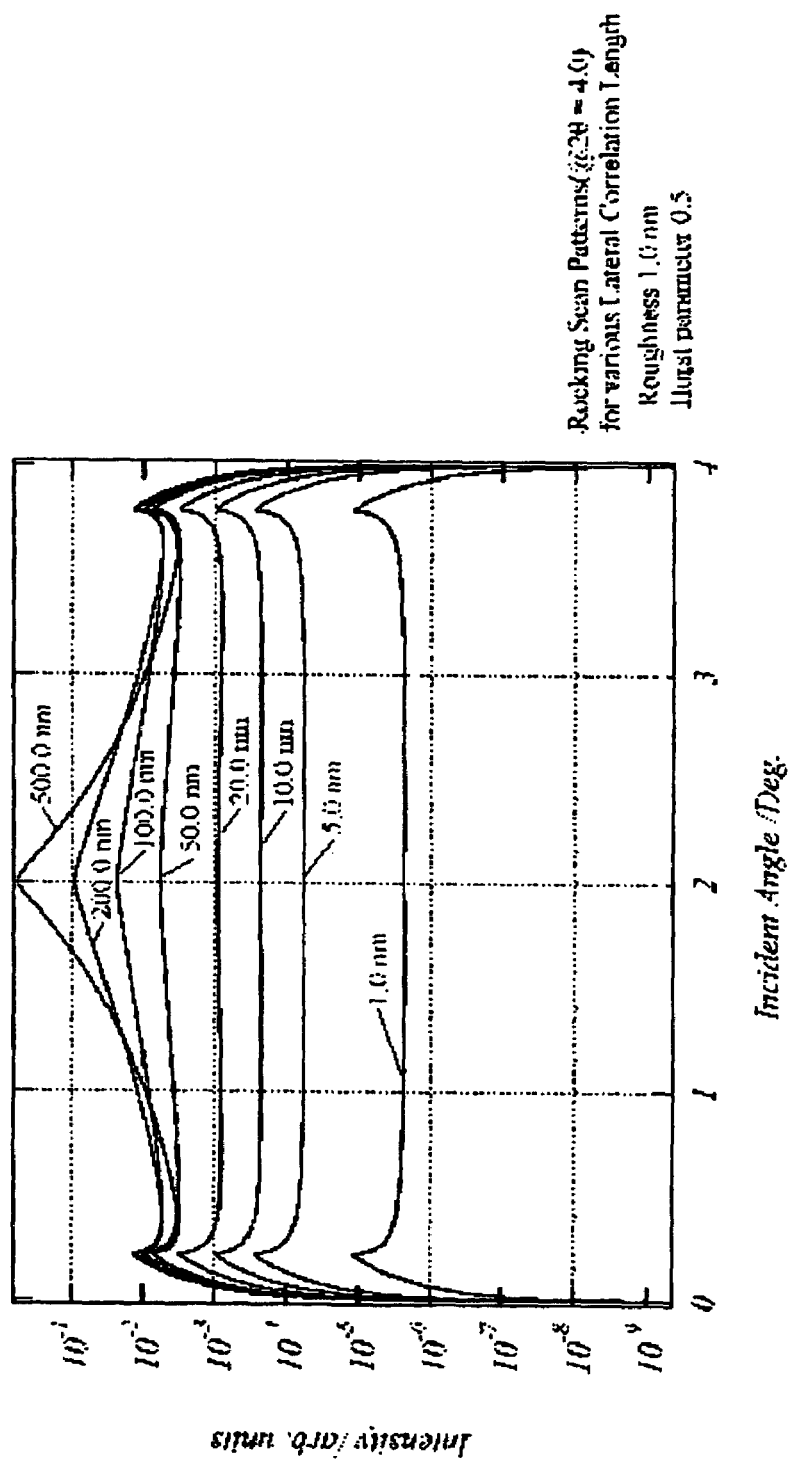
FIG. 9 is a graph showing simulated X-ray scattering curves fitted to rocking scan measurements, changing the in-plane correlation distance.
Figure 10:
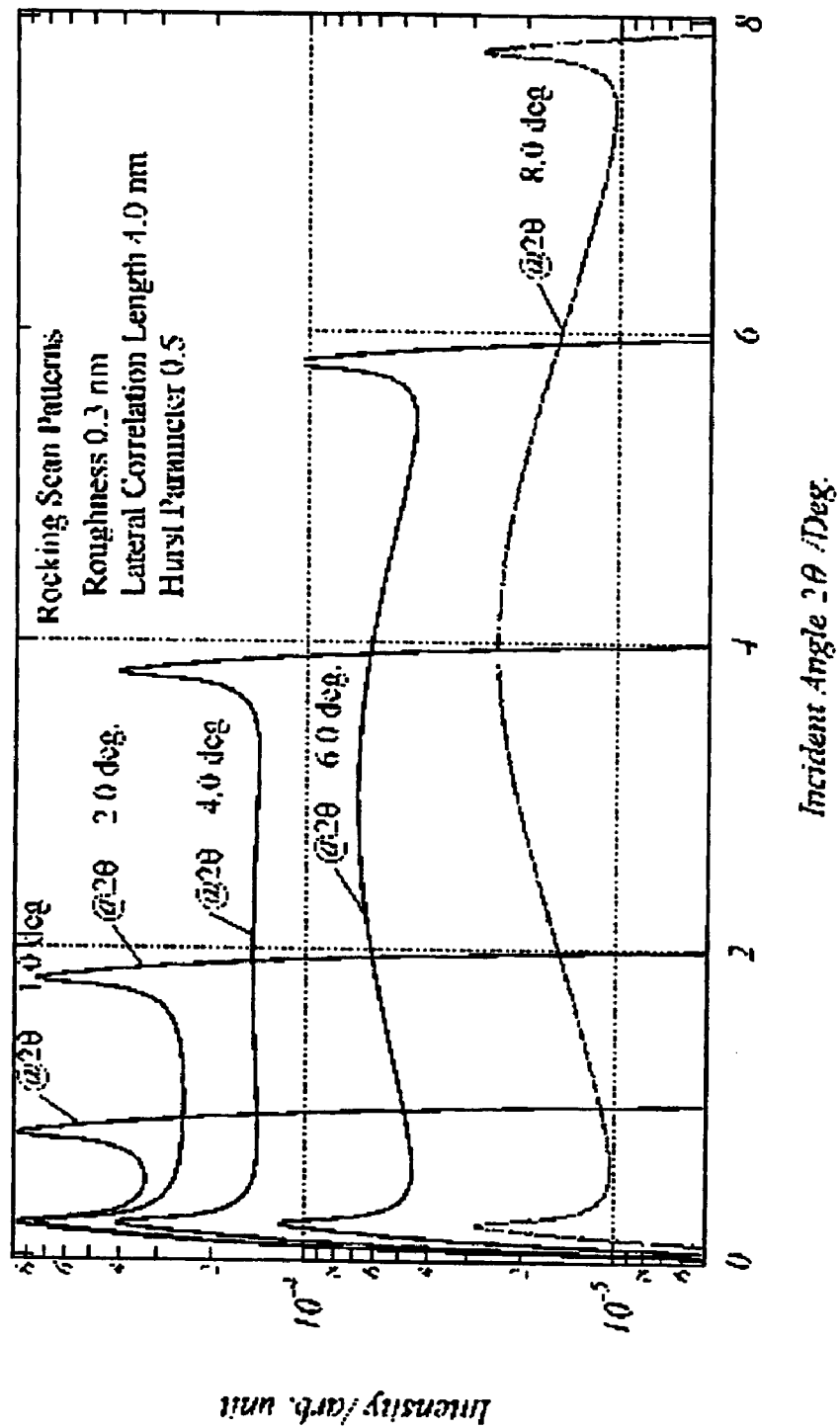
FIG. 10 is a graph showing simulated X-ray scattering curves for rocking scan measurements made changing the detector stage angle $2\theta$.

FIG. 9 shows simulated X-ray scattering curves obtained by rocking scan measurement in the case where the in-plane correlation distance is changed. In the case where the in-plane correlation distance is set at a large value, the intensity is greatly changed when the angle varies from specular reflection only slightly, i.e., by changing the in-plane scattering vector from 0 only slightly. The slope of the change corresponds to the correlation distance of in-plane electron density fluctuation, and a larger slope brings about a larger correlation distance. In the case where the in-plane correlation distance is small, on the other hand, it is necessary that the fixed angle of the detector stage angle $2\theta$ is set at such an angle that the in-plane scattering vector is greatly changed. That is, in the case where the in-plane correlation distance is small, the slope corresponding to the in-plane correlation distance is moderate, and thus it is necessary that the rocking scan measurement is carried out under such conditions that the in-plane scattering vector is greatly changed. FIG. 10 shows simulated X-ray scattering curves for rocking scan measurement in the case where the in-plane correlation distance is relatively small, and with the fixed angle of the detector stage angle $2\theta$ changed to various angles.

In an X-ray scattering curve actually measured, scattering due to pores and scattering due to interface roughness are simultaneously observed, and cannot be experimentally discriminated from each other. In the case where the interface roughness is large, and the average pore size in the film is relatively small, it is expected that at higher angles, the scattering from interface roughness is relatively weak in comparison to the scattering from pores. In this case, information of interface roughness cannot be sufficiently obtained even when the rocking scan measurement is carried out with the fixed angle of the detector stage angle $2\theta$ being set at a higher angle, and thus it is impossible to carry out adequate analysis. In the case where the average pore size is large and the interface roughness is small, on the other hand, it is almost impossible to obtain information of interface roughness even when the rocking scan measurement is carried out with the fixed angle of the detector stage angle $2\theta$ being set at a lower angle. Accordingly, it is preferred in the rocking scan measurement in this step that plural angles are selected as the fixed angle of the detector stage angle $2\theta$.

It has been demonstrated that information to determine the correlation distance of electron density fluctuation in the in-plane direction and the shape parameter thereof, i.e., the Hurst parameter, can be obtained by rocking scan measurement with the scattering vector in the in-plane direction of the surface of the specimen being changed. Further, it has been seen that it is impossible to separate scattering due to interface roughness from that due to pores in the case where the rocking scan measurement is carried out under arbitrarily set conditions. However, interface scattering on the outermost surface of the film specimen (i.e., scattering at the interface between vacuum and the outermost layer) can be obtained substantially independently as follows.

Figure 11:
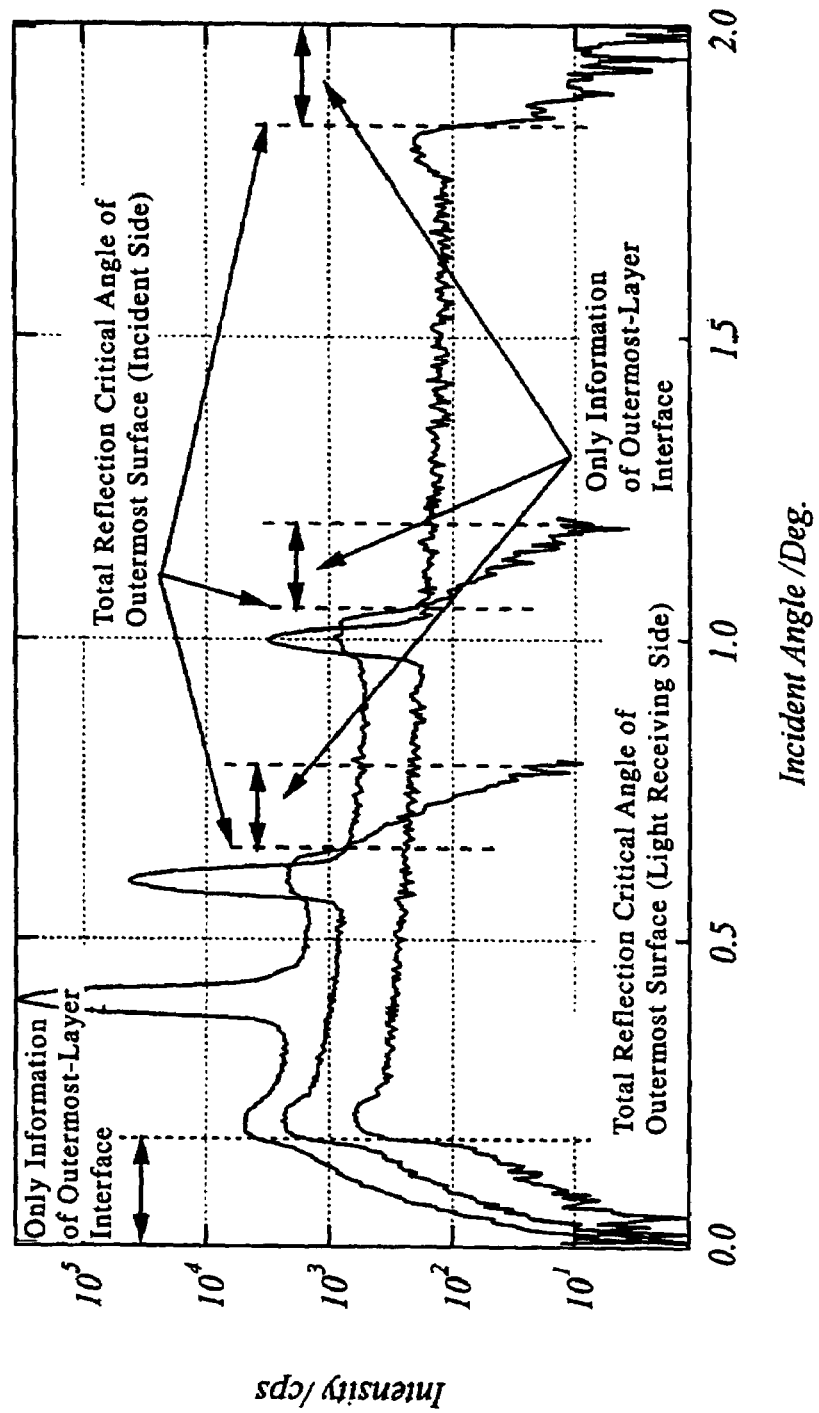
FIG. 11 is a graph showing measured X-ray scattering curves obtained by rocking scan measurement.
Figure 12:
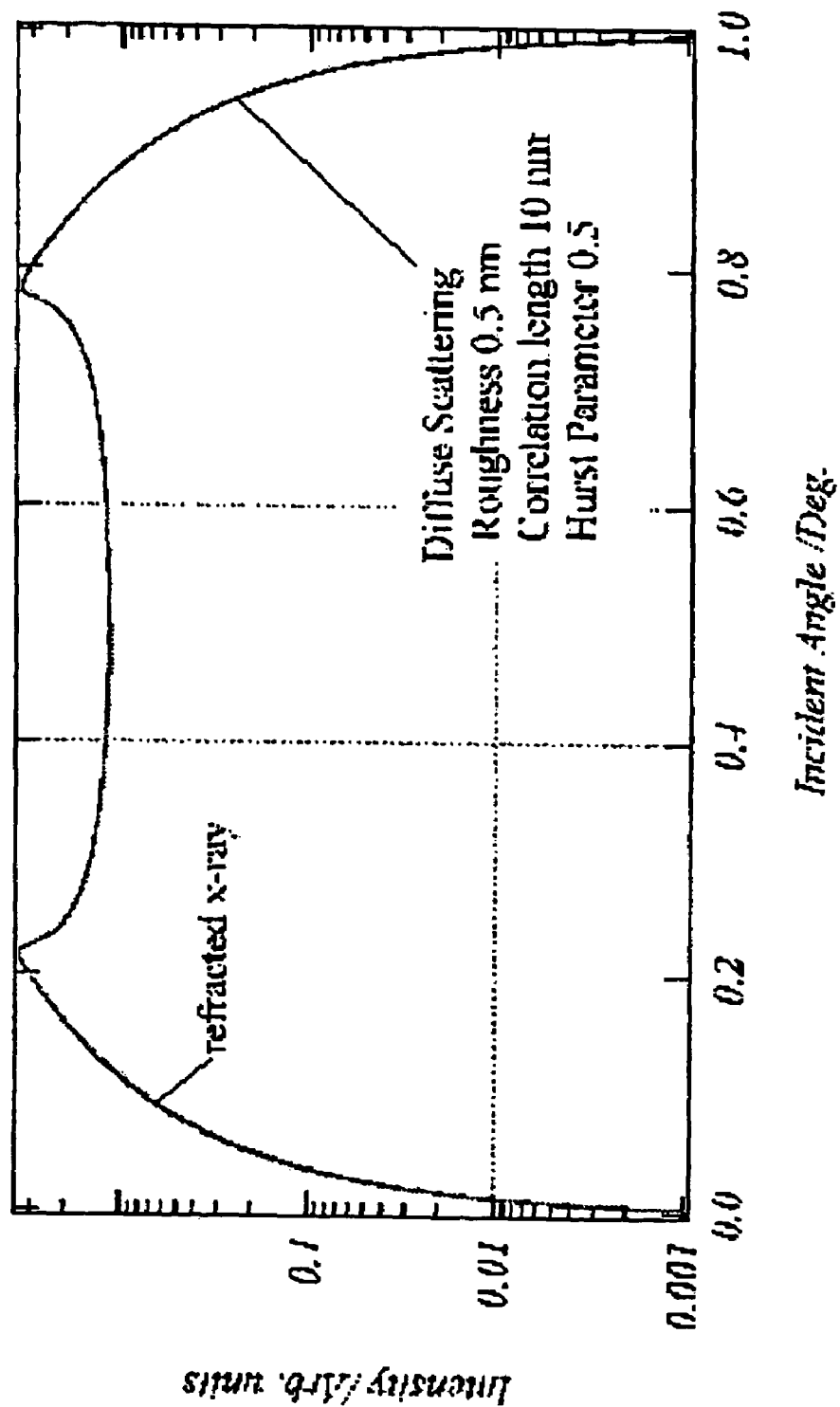
FIG. 12 is a graph showing an X-ray scattering curve by interface scattering of the outermost layer.

In the interface scattering, scattering occurs only at an interface of the film specimen. On the other hand, pore scattering occurs inside the film specimen and is observed only in the case where the conditions where the X-rays penetrate into the film specimen or the conditions where the pore scattering is reflected from the film are satisfied. These conditions are determined according to whether the incident angle and the outgoing angle of the X-ray are respectively larger or smaller than the total reflection critical angle of the film. Specifically, under the conditions where the incident angle and the outgoing angle of the X-ray are smaller than the total reflection critical angle, only the scattering of interface roughness of the outer most layer is detected (FIG. 11). Since the interface scattering is scattering generated at an interface, it is very strong when the intensity of the refraction wave at the interface is large (FIG. 12).

Figure 13:
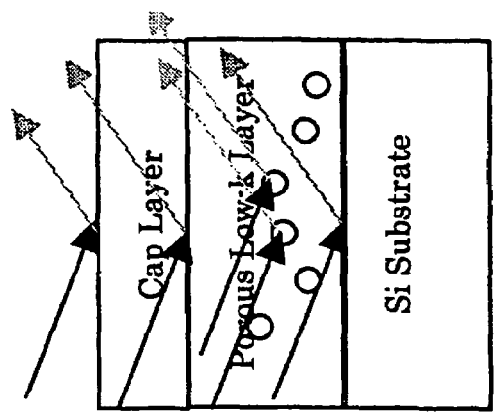
FIG. 13 is a graph showing simulated X-ray scattering curves fitted to rocking scan measurements of a multi-layer film model.
Figure 13:
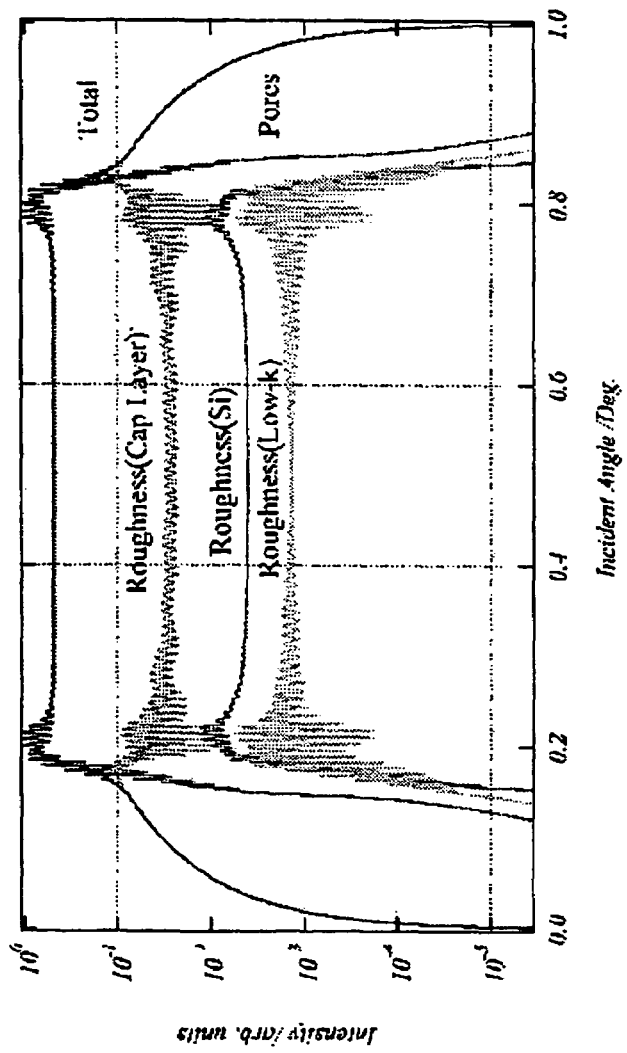

In the case where the X-ray incident angle or the X-ray outgoing angle exceeds the total reflection critical angle, the X-ray penetrates into the porous film and passes out of the porous film, and therefore, pore scattering is observed (FIG. 13).

An example of a basic embodiment of the method for analyzing a film structure according to the invention has been described hereinabove, but embodiments are not limited to the above, and of course various embodiments with variations in the details are conceivable.

The invention has the above characteristics, but it now will be described more specifically with reference to the following examples.

EXAMPLE 1

As having been described, a measured X-ray scattering curve obtained by offset scan measurement and a measured X-ray scattering curve obtained by rocking scan measurement each contains information indicating pore size distribution and information indicating interface shape. In the case of analyzing a multi-layer structure, it is difficult to determine the interface shape parameters with high accuracy since the number of the interface shape parameters is increased in proportion to the number of layers. However, structure analysis can be realized with high accuracy by handling measured data of a specimen having a multi-layer structure according to the following procedures.

(1) Roughness, the parameter of interface roughness, can be estimated to a certain extent from the result of X-ray reflectivity analysis. However, in the case where a result of X-ray reflectivity measurement is used as the initial value, it is necessary that the X-ray reflectivity analysis is sufficiently executed.

(2) Under the conditions where the X-ray incident angle or the X-ray outgoing angle is smaller than the total reflection critical angle of the outermost surface, it is possible to obtain only information of interface roughness on the outermost layer. In the data of the rocking scan measurement where plural types of settings are made, the parameter of the surface shape can be estimated in a certain extent by carrying out the fitting using the data of the angle region where the incident angle or the outgoing angle is smaller than the total reflection critical angle.

(3) In the case where a layer of a thickness of several tens of nanometers is present in a multi-layer film, scattering occurring at the upper interface of the layer interferes with scattering occurring at the lower interface thereof in the measured X-ray scattering curve, and thus a vibration structure is observed. The interference is that described by the second item of the expression (IX). According to the expression (IX), the intensity of the amplitude of the interference becomes maximum when the scattering amplitudes at the upper interface and the lower interface are equal to each other. For example, assuming a cap layer having a thickness of 40 nm on a substrate, the total scattering intensity is given from the expression (IX) by the following expression (XXI) where A represents the scattering amplitude of interface scattering occurring on the substrate, and B represents the scattering amplitude on the surface of the cap layer.

$$I_{total}=|A|^2+|B|^2+2(A^*B+B^*A) \quad (XXI)$$

Here, $|A|^2+|B|^2$ is the base and the vibration component is shown by $2(A^*B+B^*A)$, the latter being most prominent where the scattering amplitudes A and B are equal to each other.

FIGS. 14 to 17 show changes in interference scattering when the roughness of the cap layer is changed.

Figure 14:
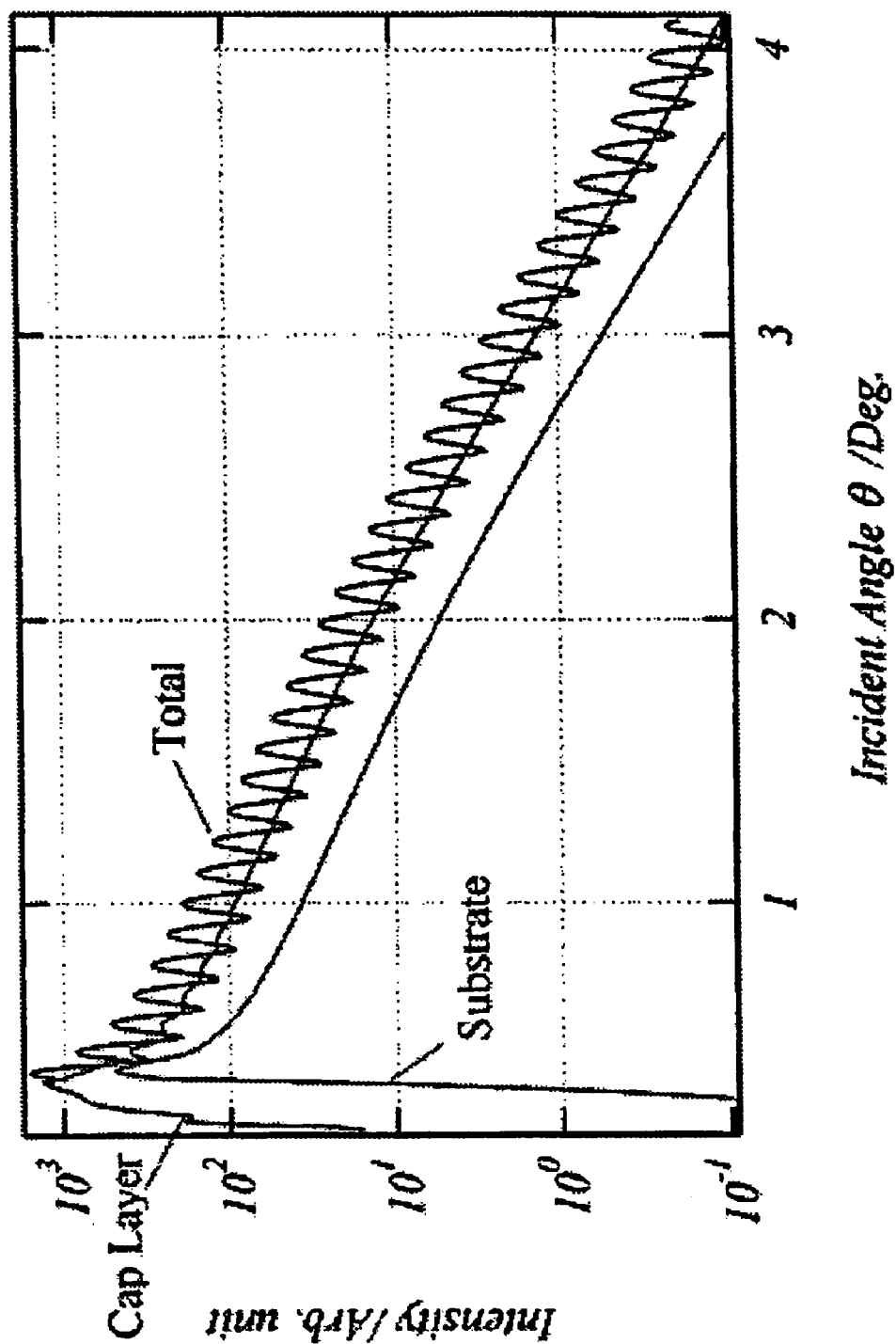
FIG. 14 is a graph showing simulated X-ray scattering curves calculated for interface scattering of a multi-layer film.

FIG. 14 shows the change in interference scattering in the case where the roughness of the substrate and that of the cap layer are set as being equal to each other as shown in following Table 1. It is clear that the vibration amplitude is substantially constant as angle increases, owing to the equal slopes.

TABLE 1

|  | σ/nm | ξ/nm | h |
|---|---|---|---|
| $SiO_2$ $\rho = 1.4\ g/cm^3$ $d = 40\ nm$ | 0.5 | 10 | 0.5 |
| Si | 0.5 | 10 | 0.5 |

Figure 15:
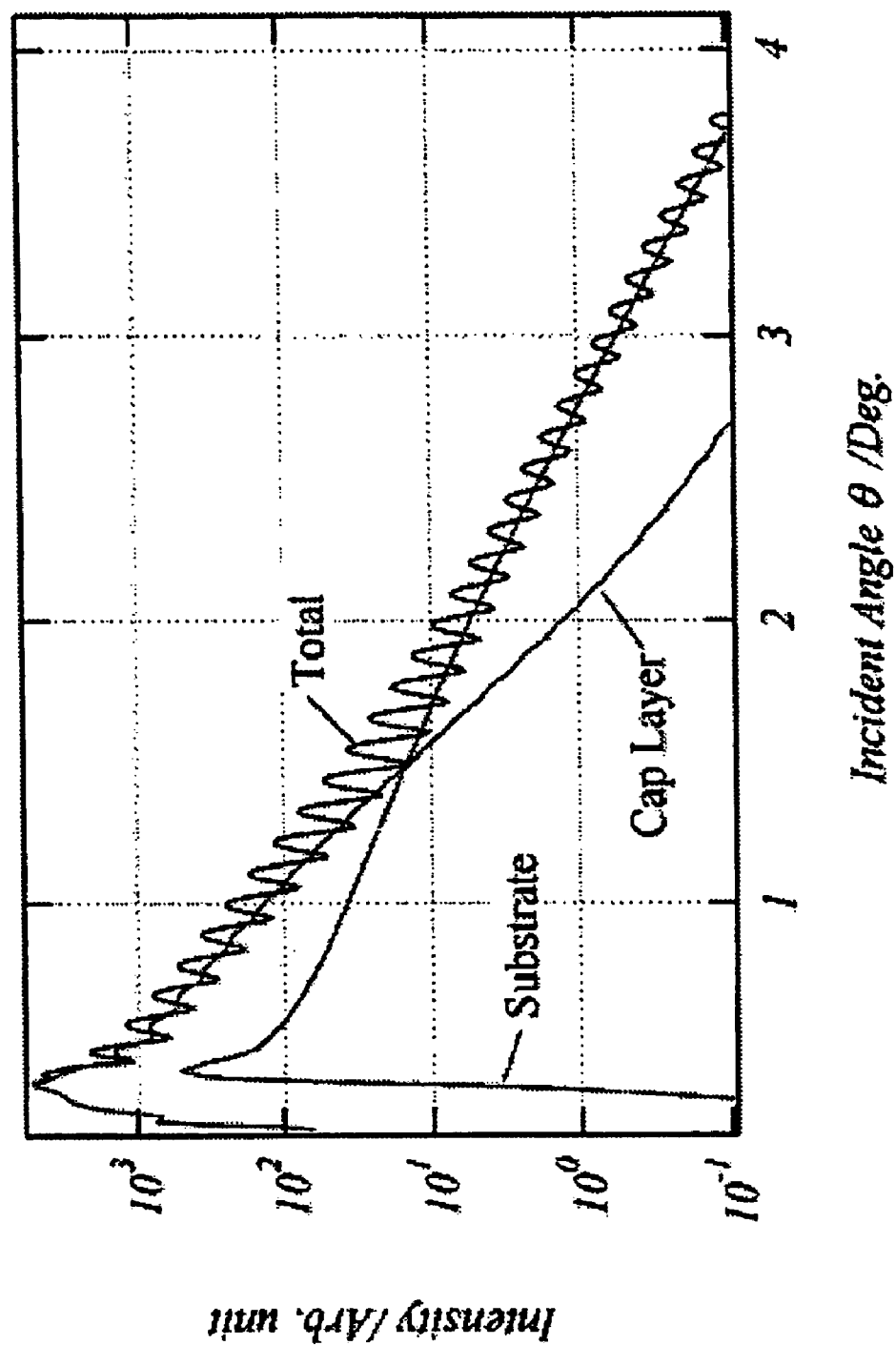
FIG. 15 is a graph showing simulated X-ray scattering curves calculated for interface scattering of a multi-layer film.

FIG. 15 shows the change in interference scattering in the case where the roughness of the substrate and that of the cap layer are slightly changed from the conditions of FIG. 14 as shown in Table 2 below. The amplitude of interference becomes the largest when the scattering intensities of the interfaces are at the same angle (in the vicinity of θ=1.5 deg), and the amplitude decreases with deviation from 1.5 deg.

TABLE 2

|  | σ/nm | ξ/nm | h |
|---|---|---|---|
| $SiO_2$ $\rho = 1.4\ g/cm^3$ $d = 40\ nm$ | 1.0 | 10 | 0.5 |
| Si | 0.5 | 10 | 0.5 |

Figure 16:
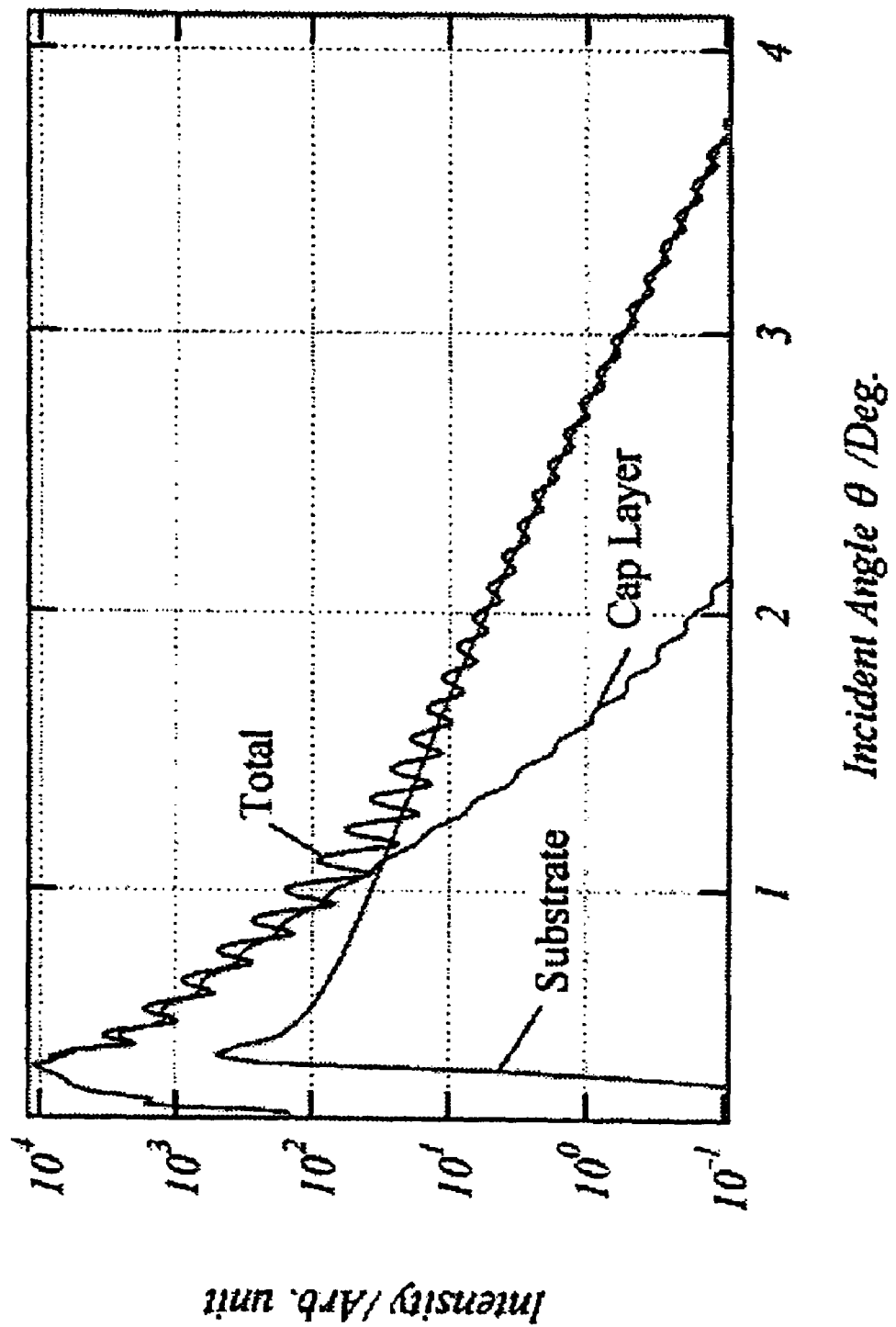
FIG. 16 is a graph showing simulated X-ray scattering curves calculated for interface scattering of a multi-layer film.

In FIG. 16, the amplitude of interference observed becomes the largest when the scattering intensities of the interfaces are at the same angle as shown in Table 3 below, similar to FIG. 15. The amplitude of interference is largely decayed at the other angles due to the large difference in roughness between the interfaces. It is seen here that a large difference in slopes of the X-ray scattering curves at the interfaces is caused by a difference in roughness between the interfaces on this scale.

TABLE 3

|  | σ/nm | ξ/nm | h |
|---|---|---|---|
| $SiO_2$ $\rho = 1.4\ g/cm^3$ $d = 40\ nm$ | 1.5 | 10 | 0.5 |
| Si | 0.5 | 10 | 0.5 |

Figure 17:
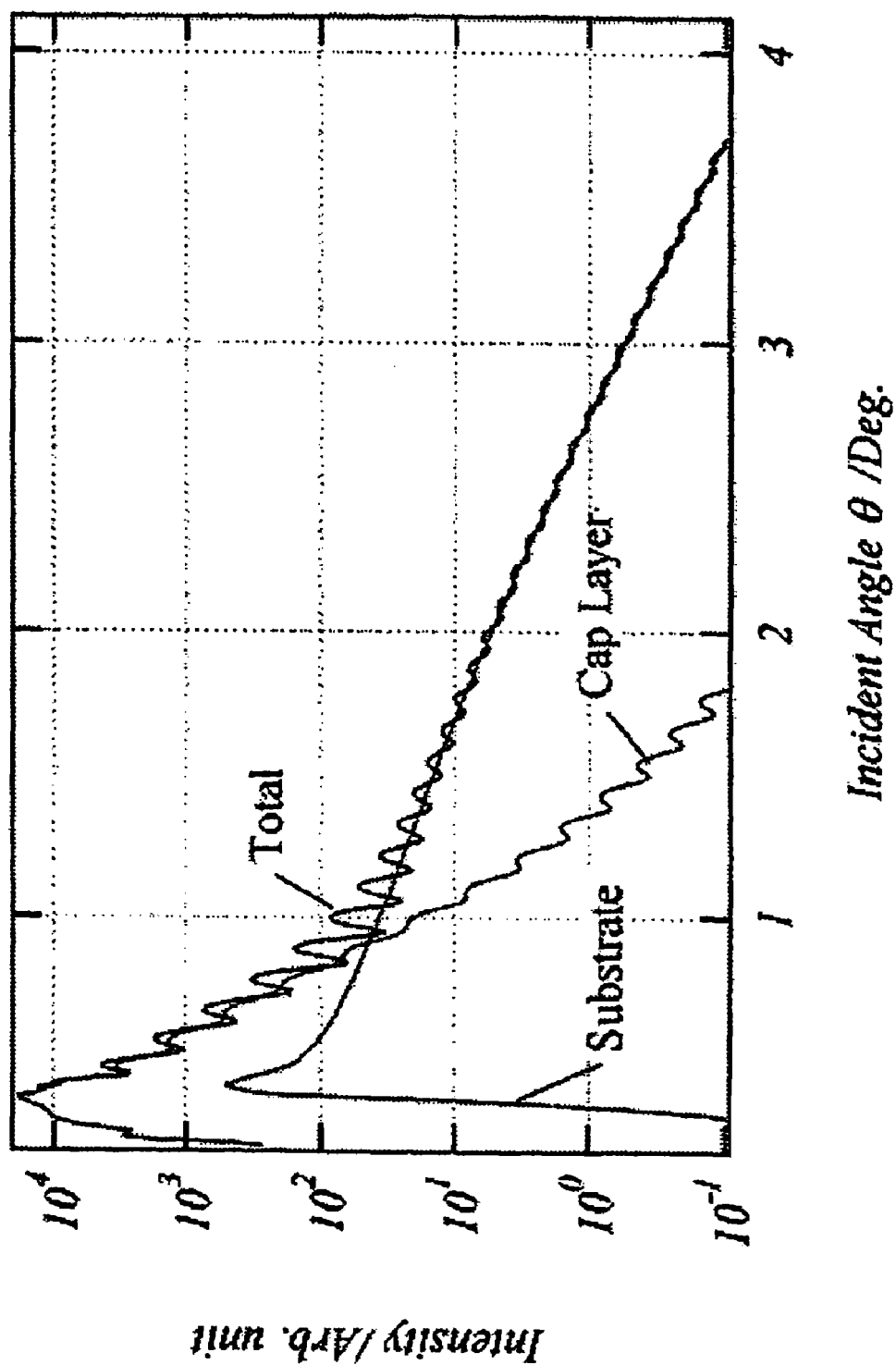
FIG. 17 is a graph showing simulated X-ray scattering curves calculated for interface scattering of a multi-layer film.
Figure 18:
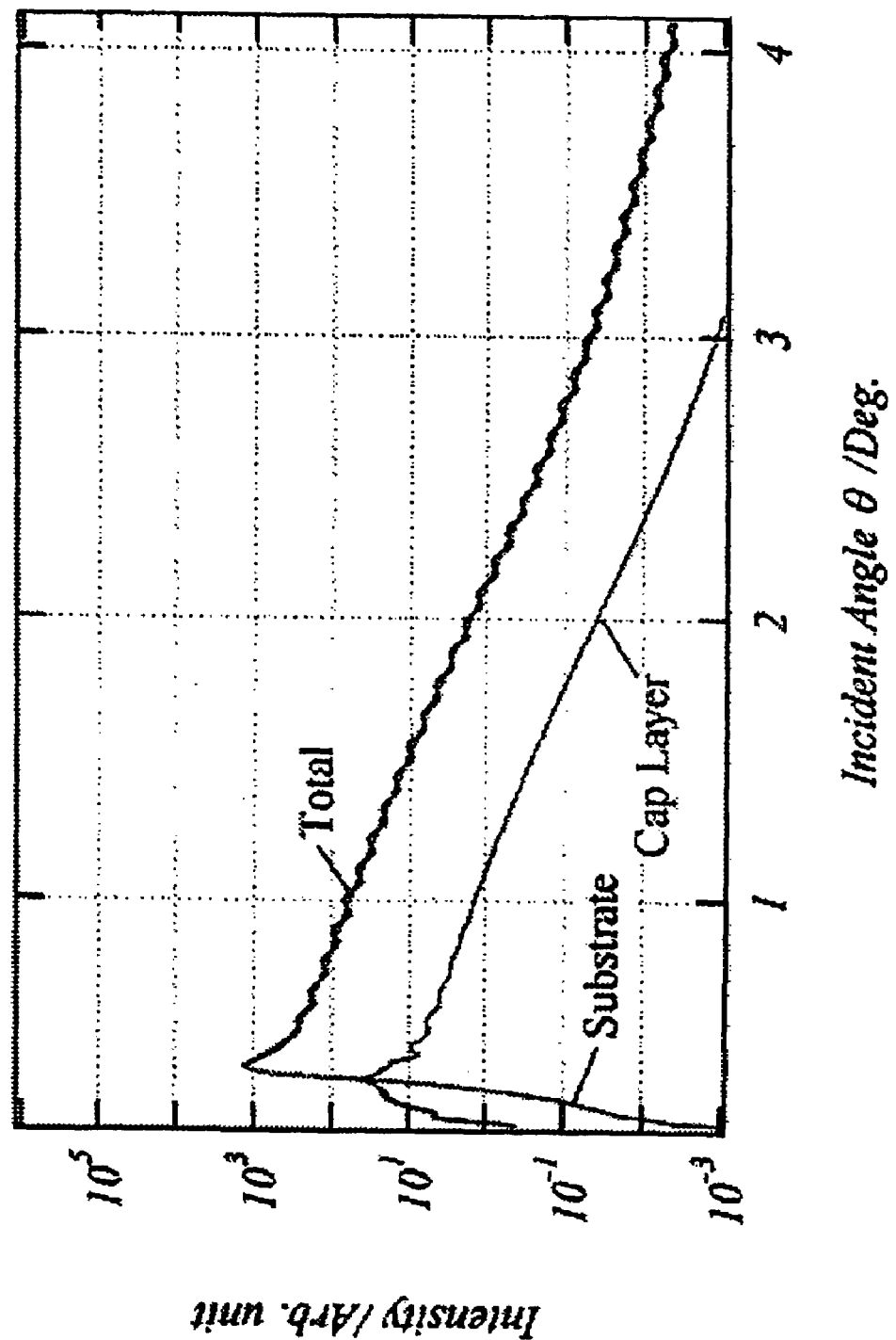
FIG. 18 is a graph showing simulated X-ray scattering curves calculated for interface scattering of a multi-layer film.
Figure 19:
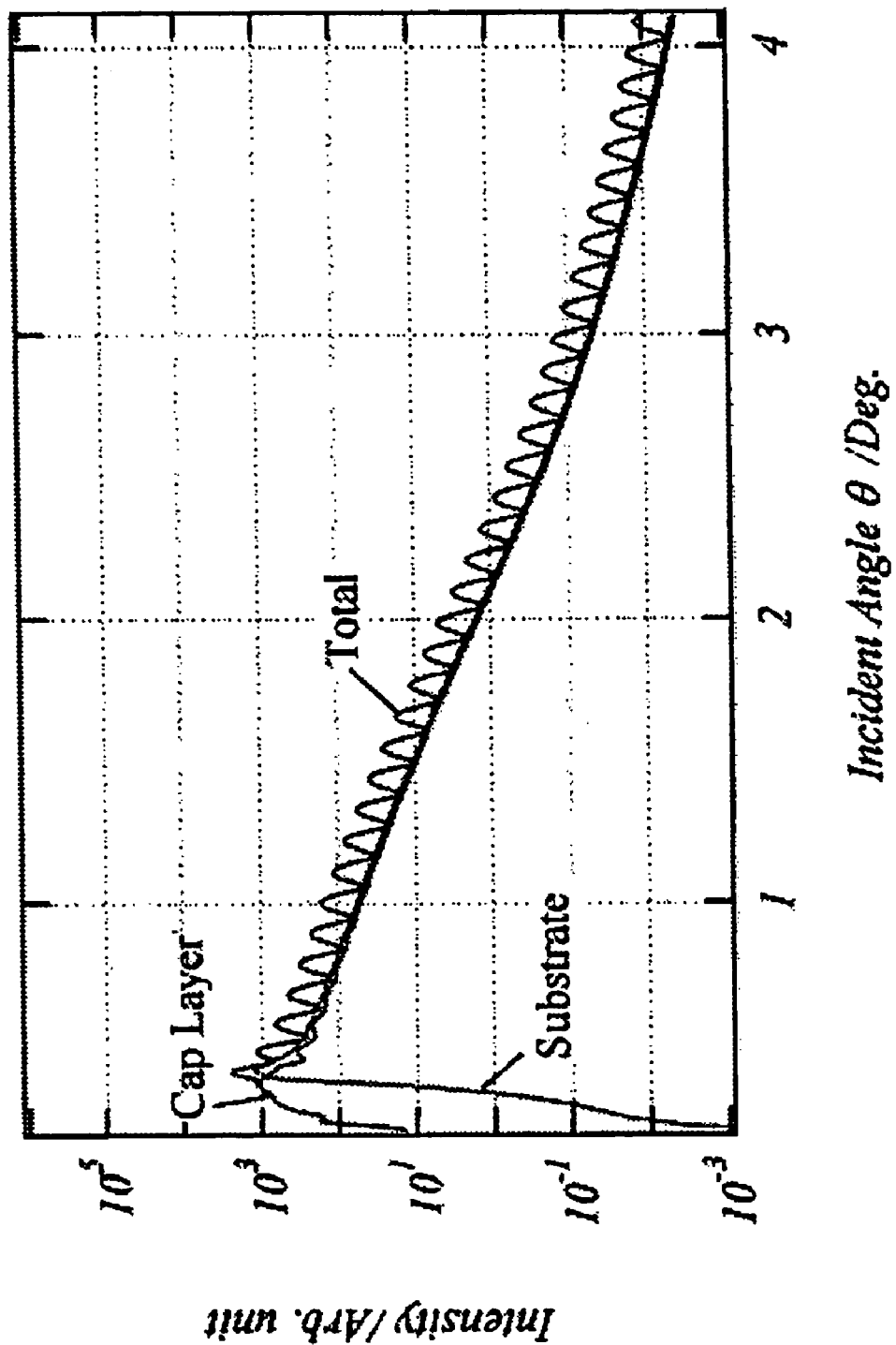
FIG. 19 is a graph showing simulated X-ray scattering curves calculated for interface scattering of a multi-layer film.
Figure 20:
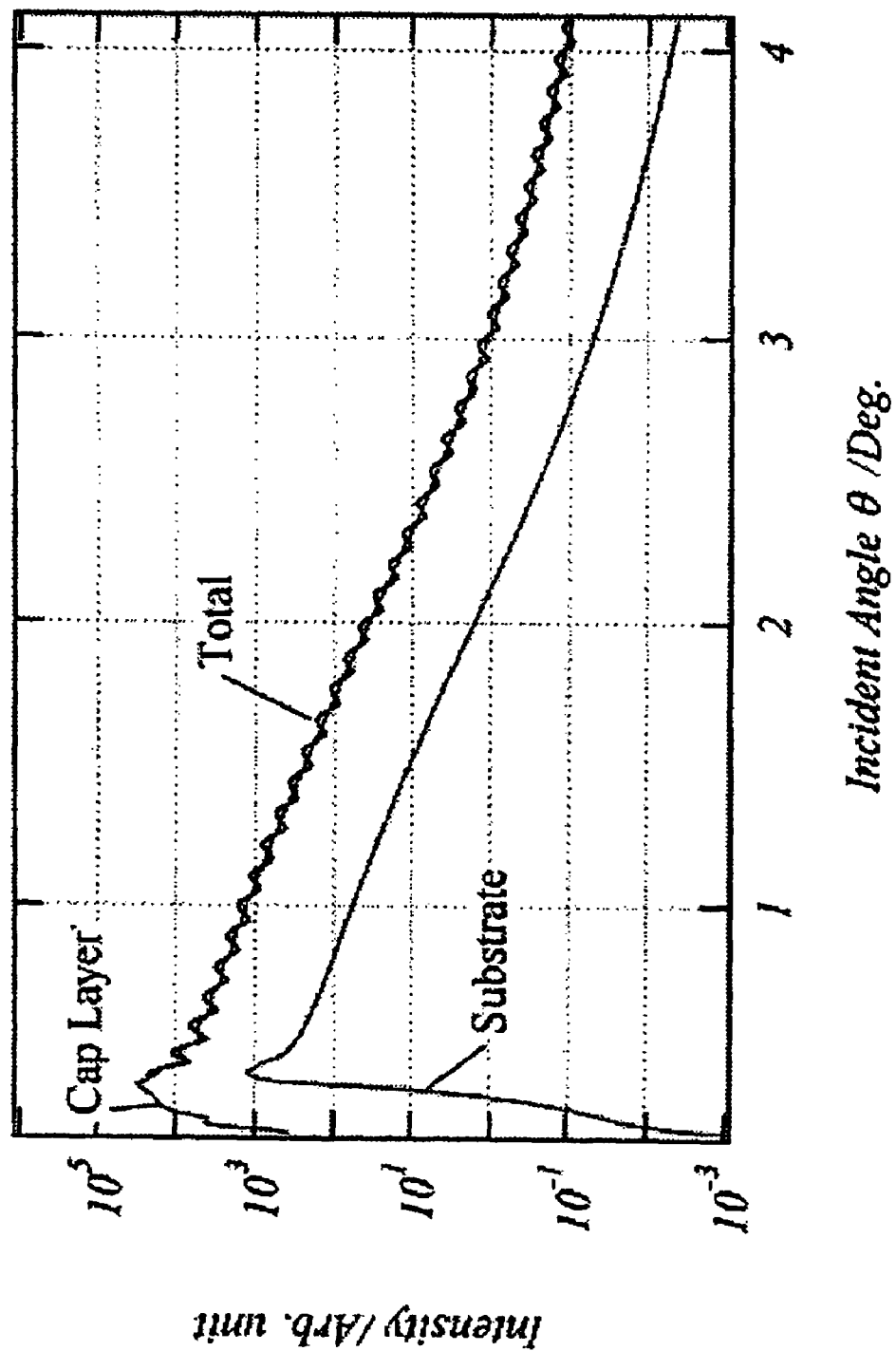
FIG. 20 is a graph showing simulated X-ray scattering curves calculated for interface scattering of a multi-layer film.
Figure 21:
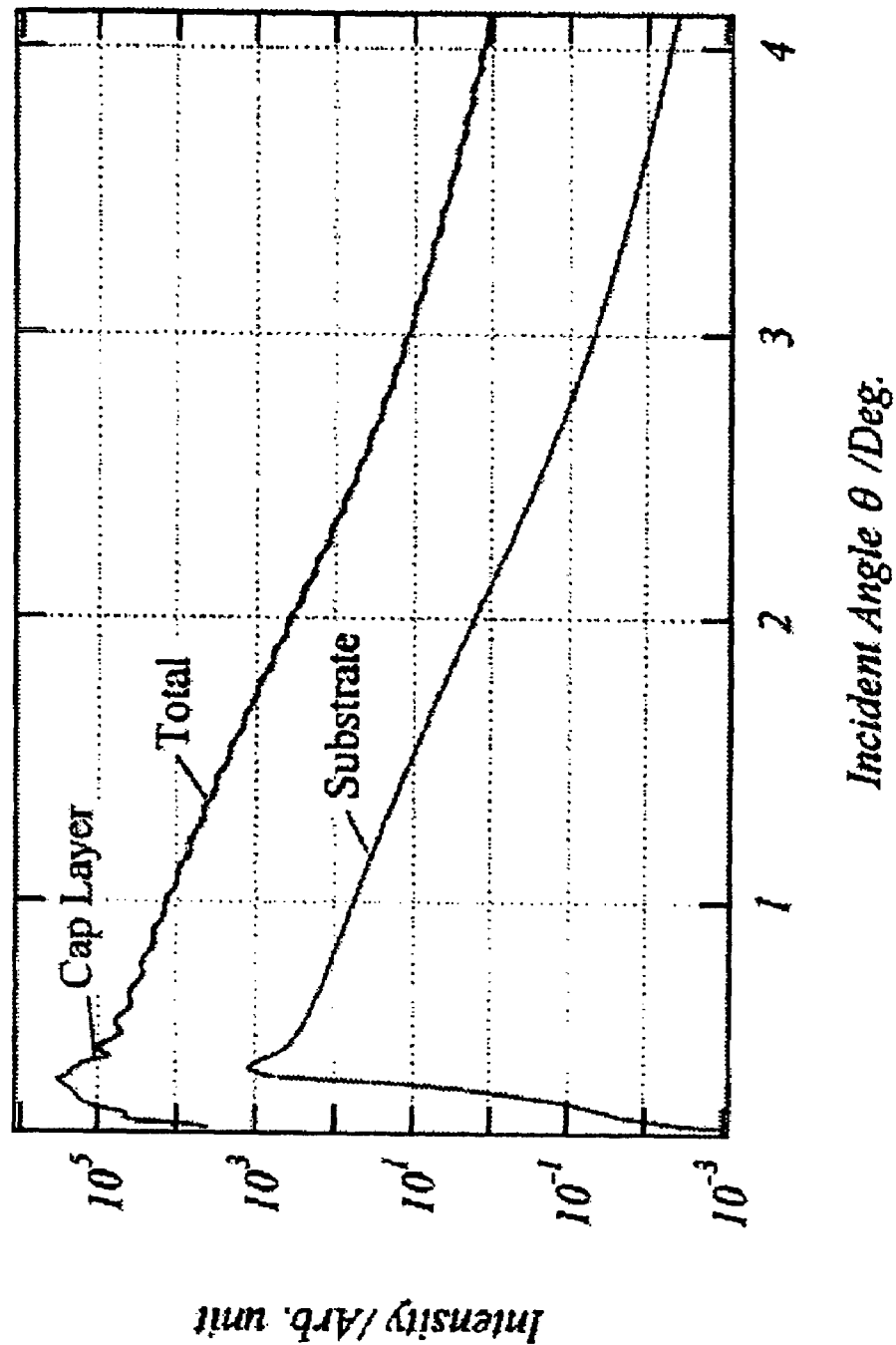
FIG. 21 is a graph showing simulated X-ray scattering curves calculated for interface scattering of a multi-layer film.

FIG. 17 shows a case where the configuration in FIG. 16 is further elicited as shown in Table 4 below. The amplitude of interference at the angle where the scattering intensities of the interfaces are equal to each other does not differ from those in FIGS. 14 to 16, but the amplitude of interference is small at the other angles due to the large difference in scattering intensities between the interfaces. As in FIG. 16, a large difference in slopes is caused by a difference in roughness between the interfaces on this scale.

TABLE 4

|  | σ/nm | ξ/nm | h |
|---|---|---|---|
| $SiO_2$ $\rho = 1.4\ g/cm^3$ $d = 40\ nm$ | 2.0 | 10 | 0.5 |
| Si | 0.5 | 10 | 0.5 |

In FIGS. 14 to 17, the curves expressing t scattering occurring at the substrate ("Substrate") correspond to $|A|^2$ in the expression (XXI), and the curves (referred to as "Cap Layer") expressing scattering occurring at the cap layer correspond to $|B|^2$ in the expression (XXI). The scattering amplitudes A and B are shown by squares of absolute values since they are complex numbers, and it is clear that the amplitude of interference becomes maximum when the scattering intensities of the interfaces are at the same angle, i.e., the two curves overlap each other. The slopes of the measured X-ray scattering intensity curves obtained by offset scan measurement of the interfaces naturally vary when the roughness of the substrate is different from that of the cap layer, and thus here the total scattering intensity is derived from two straight lines having slopes different from each other as shown in FIGS. 14 to 17. While the roughness can be determined by these slopes, the roughness can also be determined by noting the position where the amplitude of interference is changed.

(4) In the case where the ratio of the scattering amplitudes of the interfaces is changed, scattering occurring at the upper interface of the layer interferes with scattering occurring at the lower interface thereof in the measured X-ray scattering curve, and thus a vibration structure is observed. FIGS. 18 to 21 show intensities of interference in the case where the in-plane correlation distance of the interfaces is varied, and where the roughness of the substrate is equal to that of the cap layer. As in the cases shown in FIGS. 14 to 17, it is clear that in the case where the in-plane correlation distance of the cap layer is changed, i.e., the ratio of scattering amplitudes of the interfaces is changed, the amplitude of interference is increased with decrease in the difference in scattering amplitude between the interfaces. When the value of roughness is determined to a certain extent, the in-plane correlation distance can be estimated from the intensity of amplitude of interference.

(5) In the case where an arbitrary layer in the multi-layer film has a large thickness, interference between the interference scattering waves generated at the upper and lower interfaces thereof is difficult to measure due to the small vibration period thereof. Even in the case where the resolution of the optical system on the incident side or that of the optical system on the outgoing side is improved for dealing with this problem, the measurement is still difficult since the scattering probability of the interface scattering itself is small so that there is insufficient intensity. In such a case, even though the initial value of roughness can be estimated with certain accuracy from the reflectivity analysis, it is difficult to estimate the in-plane correlation distance and the initial value of the shape parameter (Hurst parameter) of roughness. According to the method for analyzing a film structure of the invention, the parameters of the interfaces of the layer having a large thickness can be obtained by the least square method when the parameters of the other layers are determined in a certain extent, but there are such cases where the parameters fall into plural local solutions due to insufficient information. In these cases, it is impossible to refine all the parameters. However, there are some cases where the issue can be solved by restricting the parameters, for example, judging parameters of the upper interface of a certain layer to be the same as those of the lower interface of the layer based on the film formation conditions and design values.

(6) As has been described, results of pore size distribution analysis of a multi-layer film based on interface scattering data and that based on pore scattering data are different. Further, it is considered that interface scattering in the in-plane direction and in the direction orthogonal to the surface exhibit different configurations. On the other hand, it is considered that the pore scattering has no anisotropy within the film in almost all cases, though it does vary depending on the material. In other words, the pore scattering can be used for an analysis of the material. In particular, the surface/interface scattering is continuously increased with the approach of the X-ray incident angle or the X-ray outgoing angle to the vicinity of the total reflection critical angle of the outermost surface of the film, but the pore scattering is not observed unless the X-ray incident angle or the X-ray outgoing angle exceeds the total reflection critical angle. Furthermore, in the pore scattering, the scattering intensity is suddenly increased immediately after one of these angles exceeds the total reflection critical angle. Moreover rocking scan measurement of the pore scattering provides a flat X-ray scattering curve as opposed to interface scattering, unless the average pore diameter is extremely large. Accordingly, the pore size distribution analysis utilizing the respective characteristics of the pore scattering and the interface scattering is not difficult.

As described, the method for analyzing a film structure of the invention can also be applied to a multi-layer film specimen. The characteristic features appearing in the case where the method for analyzing a film structure of the invention is applied to a multi-layer film specimen as described in detail hereinabove are summarized below.

(A) The surface scattering has characteristics that are dependent on the intensity of the surface refraction wave, and thus the surface structure can be relatively easily determined.

(B) The structures of the respective interfaces of a multi-layer film specimen can be evaluated by utilizing the interference component of the interface scattering shown by the second item of the expression (IX).

(C) The pore size of a porous film can be analyzed by utilizing such characteristics that the pore scattering is suddenly increased immediately after exceeding the total reflection critical angle of the porous layer.

EXAMPLE 2

A multi-layer film containing a substrate formed thereon with a porous film layer, a cap layer and an oxide film layer in this order from the bottom is prepared as a specimen, and results of analysis of the pore size of the porous layer and the interface shape of the multi-layer film are shown below.

Figure 22:
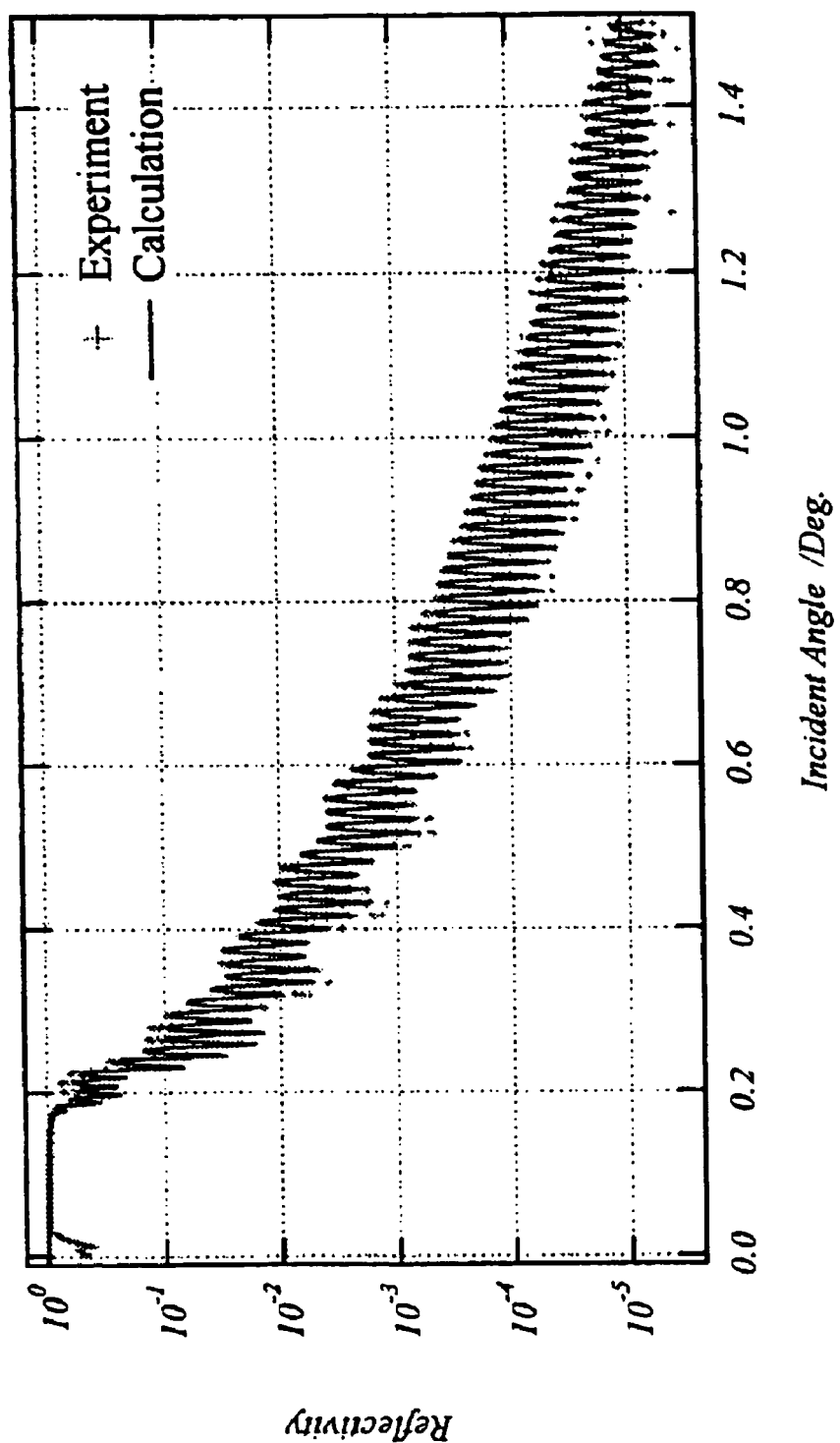
FIG. 22 is a graph showing results of X-ray reflectivity analysis carried out in the example of the invention.
Figure 23:
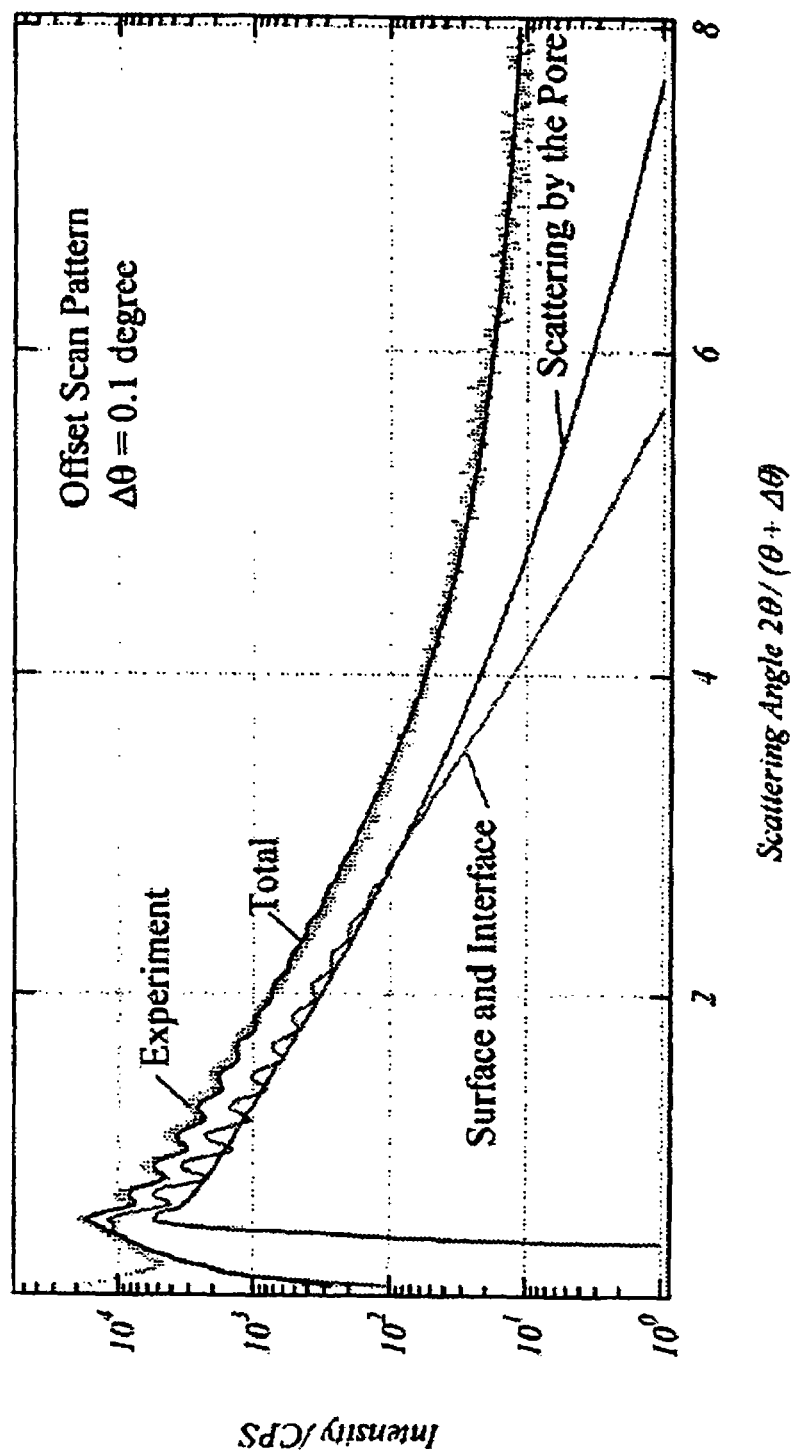
FIG. 23 is a graph showing a result of fitting to a measured X-ray scattering curve of rocking scan measurement obtained in the example of the invention.
Figure 24:
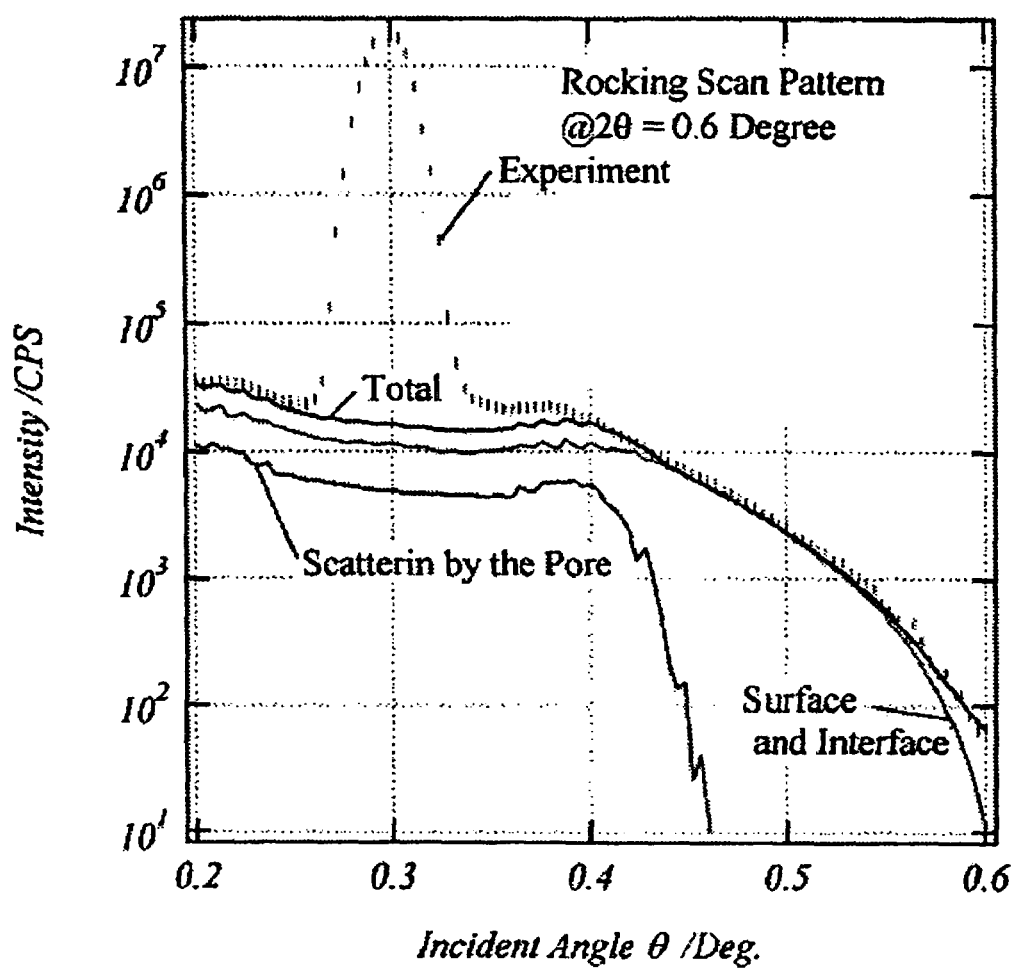
FIG. 24 is a graph showing a result of fitting to a measured X-ray scattering curve of rocking scan measurement obtained in the example of the invention.
Figure 25:
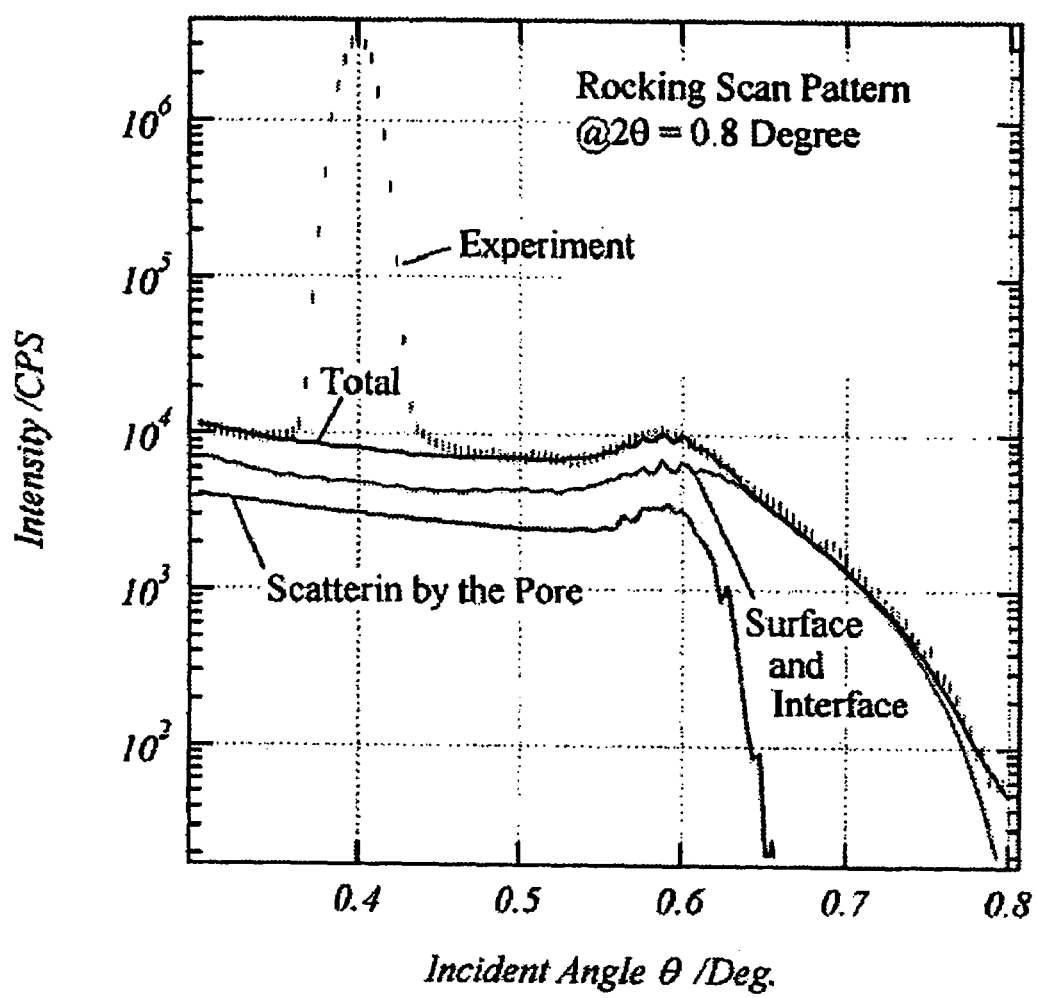
FIG. 25 is a graph showing a result of fitting to a measured X-ray scattering curve of rocking scan measurement obtained in the example of the invention.
Figure 26:
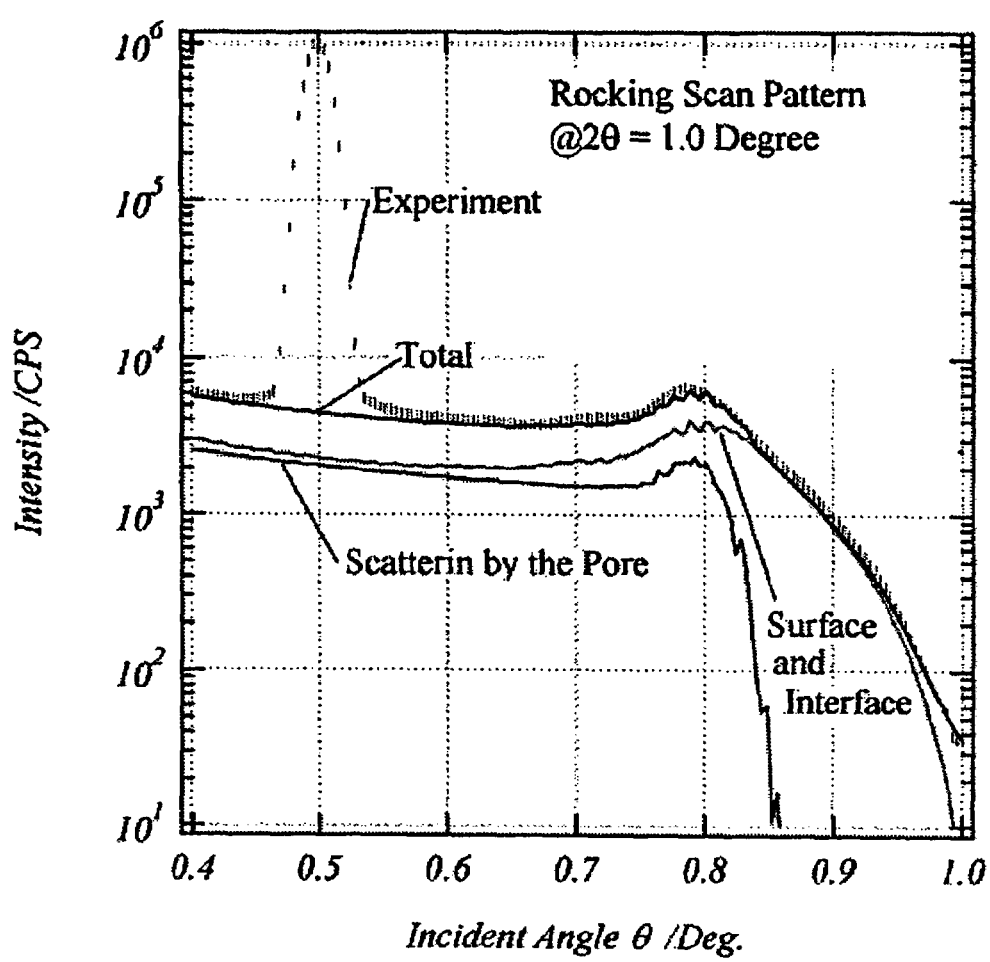
FIG. 26 is a graph showing a result of fitting to a measured X-ray scattering curve of rocking scan measurement obtained in the example of the invention.
Figure 27:
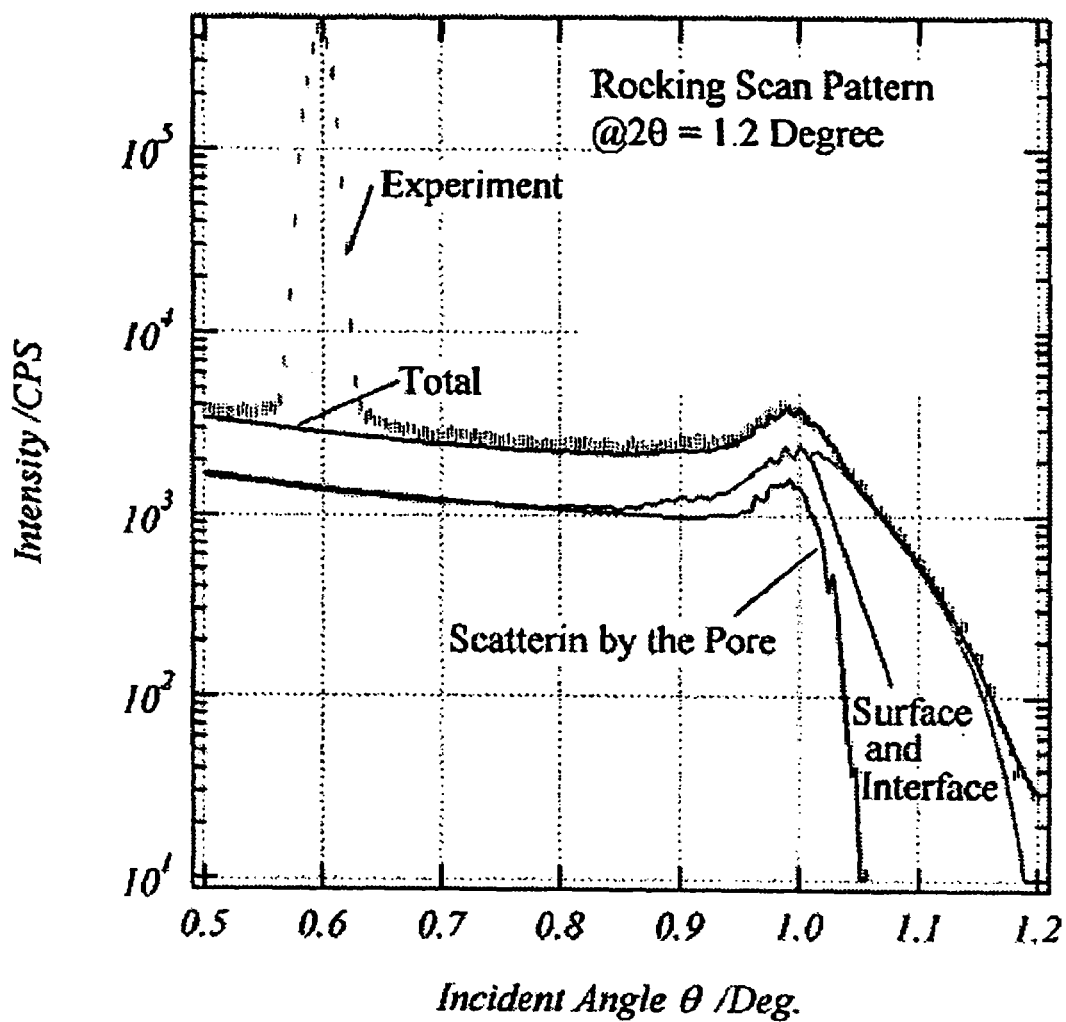
FIG. 27 is a graph showing a result of fitting to a measured X-ray scattering curve of rocking scan measurement obtained in the example of the invention.

X-ray reflectivity measurement is firstly carried out to obtain the X-ray reflection curve shown in FIG. 22. As a result of X-ray reflectivity analysis using the X-ray reflectivity curve, density and thickness are obtained as shown in Table 5 below.

TABLE 5

| | Density (g/cc) | Thickness (nm) | Roughness (nm) | Remarks |
|---|---|---|---|---|
| $SiO_2$ | 2.186 | 4.670 | 0.7 | high density layer |
| $Si_2O_3CH_3$ | 1.463 | 41.0 | 2.0–3.0* | cap layer |
| $Si_2O_3CH_3$ | 1.047 | 201.0 | 1.5 | porous layer |
| Si | 2.33 | — | 0.6 | substrate |

*An approximate value is shown because the profile is not significantly influenced even when the roughness of the cap layer is changed within a range of from 2.0 to 3.0 nm.

The X-ray eigenstate in the film is defined based on the values of density and thickness obtained through the X-ray reflectivity analysis, and the X-ray diffuse scattering measurement data is analyzed, whereby the shapes of the respective interfaces and the pore size of the porous layer of the multi-layer film are analyzed. As the initial value of roughness, the analyzed value of the X-ray reflectivity analysis is used.

Figure 28:
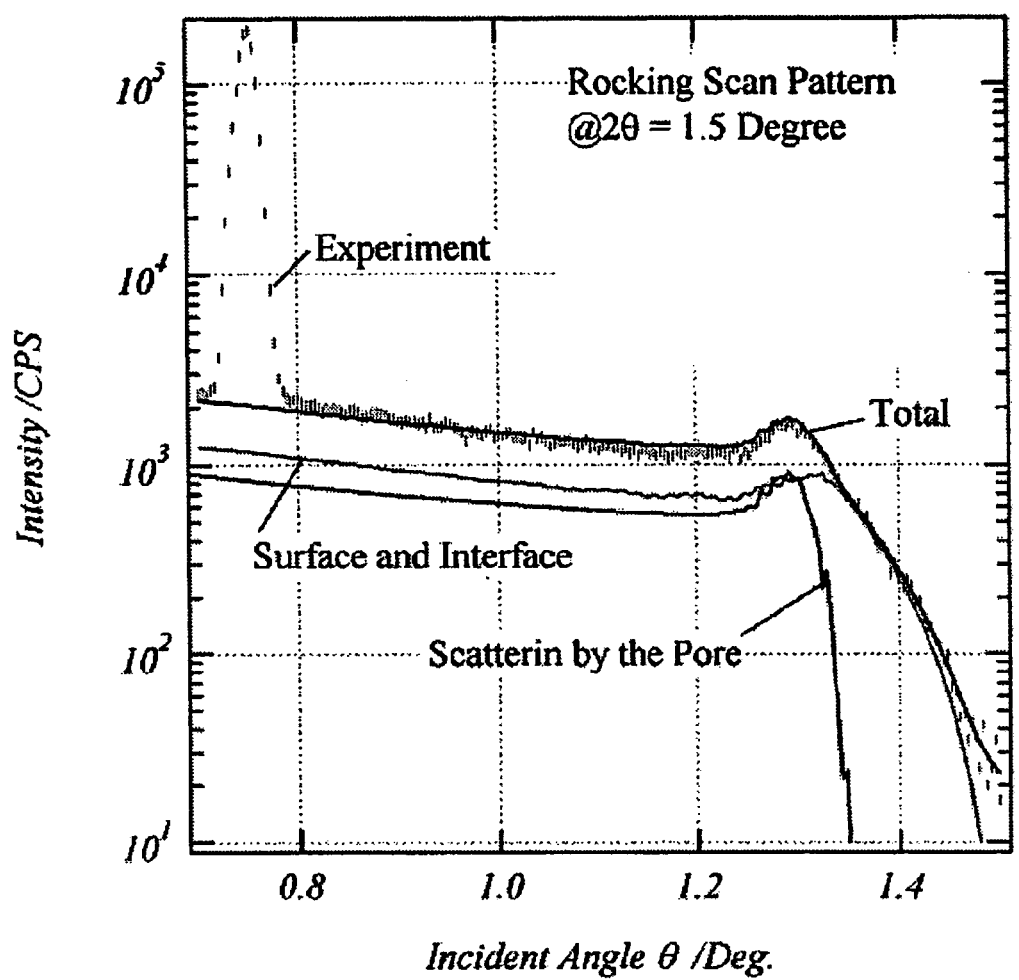
FIG. 28 is a graph showing a result of fitting to a measured X-ray scattering curve of rocking scan measurement obtained in the example of the invention.
Figure 29:
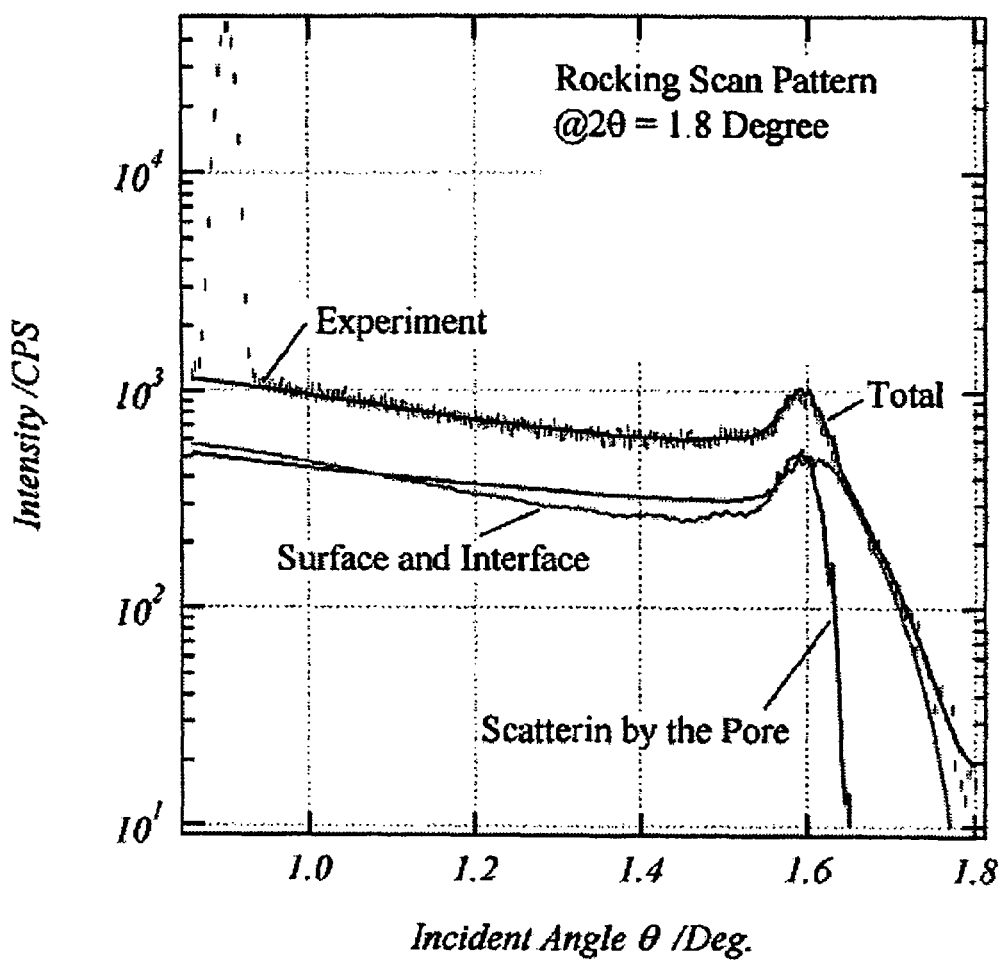
FIG. 29 is a graph showing a result of fitting to a measured X-ray scattering curve of rocking scan measurement obtained in the example of the invention.
Figure 30:
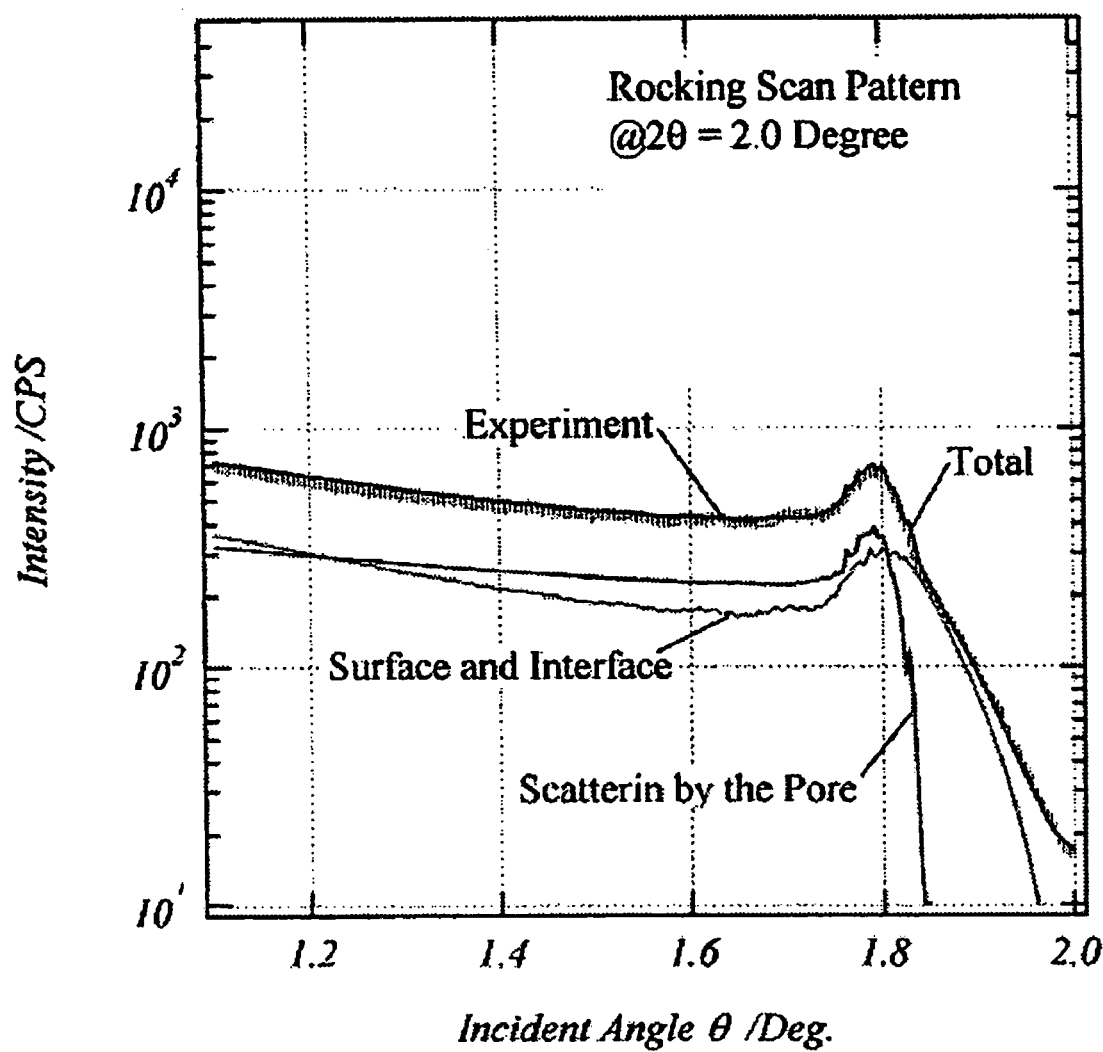
FIG. 30 is a graph showing a result of fitting to a measured X-ray scattering curve of rocking scan measurement obtained in the example of the invention.
Figure 31:
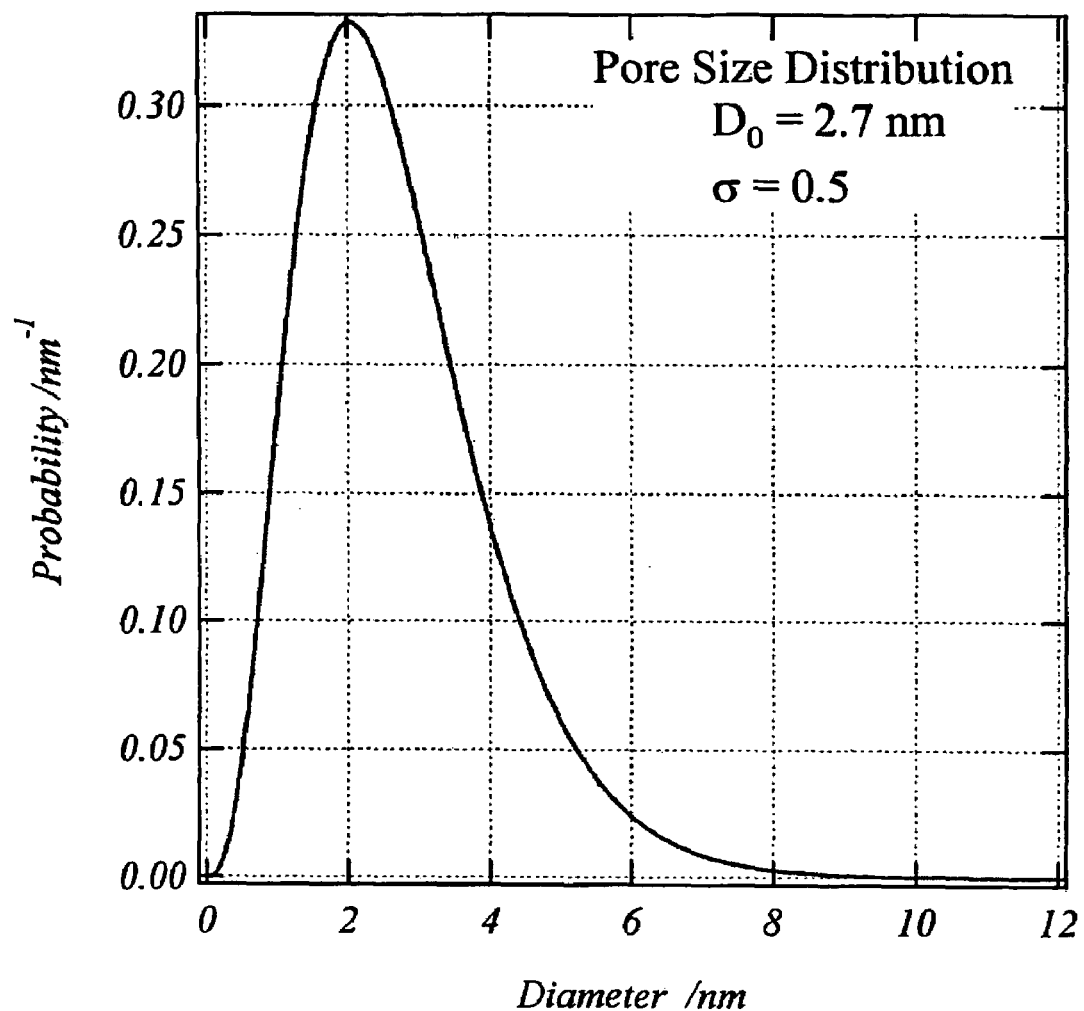
FIG. 31 is a graph showing pore size distribution of a porous layer analyzed in the example of the invention.

The fitting of the simulated X-ray scattering curve to measured X-ray scattering curves obtained by offset scan measurement with the incident angle and the outgoing angle being deviated by 0.1° and to measured X-ray scattering curves obtained by seven kinds of rocking scan measurement with 2θ being fixed to 0.6, 0.8, 1.0, 1.2, 1.5, 1.8 and 2.0 is carried out. Results of the fitting corresponding to the respective measured X-ray scattering curves are shown in FIGS. 28 to 30. The pore size distribution in the porous layer thus analyzed is shown in FIG. 31. Analysis results obtained by the fitting are shown in Table 6 below.

TABLE 6

| | Structure analysis of interface roughness | | | Pore size analysis | |
|---|---|---|---|---|---|
| | σ/nm | ξ/nm | h | D0/nm | σ/(norm. variance) |
| $SiO_2$ | 0.8 | 1.6 | 0.20 | — | — |
| $Si_2O_3CH_3$ | 2.0 | 4.1 | 0.30 | — | — |
| $Si_2O_3CH_3$ | 1.5 | 7.9 | 0.30 | 2.7 | 0.5 |
| Si | 0.5 | 6.7 | 0.35 | — | — |

Analysis of a film structure, such as analysis of pore size distribution, has been conventionally carried out by using only one measured X-ray scattering curve obtained by offset scan measurement, but in the case where interface roughness scattering is observed with an intensity that cannot be ignored, it is necessary that the interface scattering be taken into consideration. The interface scattering exhibits a characteristic in a measured X-ray scattering curve obtained by rocking scan measurement, and therefore, in the method for analyzing a film structure according to the invention, the pore size distribution analysis and the interface shape analysis are simultaneously carried out by using the X-ray scattering curves obtained by offset scan measurement and the X-ray scattering curves obtained by plural kinds of rocking scan measurement. In this example, it is expected that the analysis result of the interface shape of the cap layer contains some errors due to the low influence of the roughness of the cap layer on the X-ray reflectivity and the diffuse scattering pattern. However, the pore scattering and the interface scattering provide different shapes of measured X-ray scattering curves as described above, and therefore, it is considered that a large error is not contained in the analysis result of pore size distribution.

According to the invention, a method for analyzing a film structure and an apparatus therefor are provided that realize simultaneous analysis of a shape of an interface and a pore size of a specimen, and can be applied to a specimen having a multi-layer structure.

According to the method for analyzing a film structure and the apparatus therefor of the invention, the shape of an interface of a specimen and the pore size of a specimen can be analyzed even when the specimen examined is a multi-layer specimen, without changing the structure of a conventional apparatus for measuring X-ray reflectivity. Therefore, it is considered that the method for analyzing a film structure and the apparatus therefor of the invention contribute to determination of characteristics during development of various kinds of functional materials, and practical applications thereof are strongly expected.

What is claimed is:

1. A method for analyzing a film structure, the method comprising:

fitting a simulated X-ray scattering curve obtained by simulation calculation to a measured X-ray scattering intensity curve obtained by emitting X-rays onto a surface of a film specimen having a single layer or multi-layer structure at an angle in a vicinity of a critical angle to the surface, by varying at least one parameter characterizing a physical property of the film specimen; and obtaining optimum values of parameters providing a minimum difference between the measured X-ray scattering intensity curve and the simulated X-ray scattering curve, so as to determine the structure of the film specimen, wherein plurality of combinations of incident angle and outgoing angle to the surface of the film specimen are set such that there is no correlation between the incident angle and the outgoing angle, and the measured X-ray scattering intensity curve is obtained by measuring an X-ray intensity for each of the respective combinations of incident angle and outgoing angle.

2. A method for analyzing a film structure, the method comprising:

fitting a simulated X-ray scattering curve obtained by simulation calculation to a measured X-ray scattering intensity curve obtained by emitting X-rays onto a surface of a film specimen having a single layer or multi-layer structure at an angle in a vicinity of a critical angle to the surface, by varying at least one parameter characterizing a physical property of the film specimen; and obtaining optimum values of parameters providing a minimum difference between the measured X-ray scattering intensity curve and the simulated X-ray scattering curve, so as to determine the structure of the film specimen, wherein the measured X-ray scattering intensity curve is obtained by at least two kinds of measurements selected from among offset scan measurement, rocking scan measurement and detector scan measurement.

3. The method for analyzing a film structure as claimed in claim 2, wherein the simulated X-ray scattering curve is obtained by simulation calculation and by varying parameters relating to interface roughness of the surface of the film specimen and pore size inside the film specimen and is fitted to the measured X-ray scattering intensity curve that is obtained by the offset scan measurement, and the optimum values of the parameters providing the minimum difference between the measured X-ray scattering intensity curve and the simulated X-ray scattering curve are obtained, so as to determine the structure of the film specimen.

4. An apparatus for analyzing a film structure, the apparatus comprising:

means for fitting a simulated X-ray scattering curve obtained by simulation calculation to a measured X-ray scattering intensity curve obtained by emitting an X-ray onto a surface of a film specimen having a single layer or multi-layer structure at an angle in a vicinity of a critical angle to the surface, by varying at least one parameter characterizing a physical property of the film specimen; and means for obtaining optimum values of parameters providing a minimum difference between the measured X-ray scattering intensity curve and the simulated X-ray scattering curve, so as to determine the structure of the film specimen, wherein plurality of combinations of incident angle and outgoing angle to the surface of the film specimen are set such that there is no correlation between the incident angle and the outgoing angle, and the measured X-ray scattering intensity curve is obtained by measuring an X-ray intensity for each of the respective combinations of incident angle and outgoing angle.

5. An apparatus for analyzing a film structure, the apparatus comprising:

means for fitting a simulated X-ray scattering curve obtained by simulation calculation to a measured X-ray scattering intensity curve obtained by emitting an X-ray onto a surface of a film specimen having a single layer or multi-layer structure at an angle in a vicinity of a critical angle to the surface, by varying at least one parameter characterizing a physical property of the film specimen; and means for obtaining optimum values of parameters providing a minimum difference between the measured X-ray scattering intensity curve and the simulated X-ray scattering curve, so as to determine the structure of the film specimen, wherein the measured X-ray scattering intensity curve is obtained by at least two kinds of measurements selected from offset scan measurement, rocking scan measurement and detector scan measurement.

6. The apparatus for analyzing a film structure as claimed in claim 5, wherein the simulated X-ray scattering curve is obtained by simulation calculation and by varying parameters relating to interface roughness of the surface of the film specimen and pore size inside the film specimen and is fitted to the measured X-ray scattering intensity curve that is obtained by the offset scan measurement, and the optimum values of the parameters providing the minimum difference between the measured X-ray scattering intensity curve and the simulated X-ray scattering curve are obtained, so as to determine the structure of the film specimen.

* * * * *